(12) United States Patent
Jeong et al.

(10) Patent No.: US 11,684,894 B2
(45) Date of Patent: Jun. 27, 2023

(54) IN SITU FABRICATION OF METAL-ORGANIC FRAMEWORK FILMS AND MIXED-MATRIX MEMBRANES

(71) Applicant: Texas A&M University, College Station, TX (US)

(72) Inventors: Hae-Kwon Jeong, College Station, TX (US); Mohamad Rezi Abdul Hamid, Perak (MY)

(73) Assignee: Texas A&M University, College Station, TX (US)

( * ) Notice: Subject to any disclaimer, the term of this patent is extended or adjusted under 35 U.S.C. 154(b) by 161 days.

(21) Appl. No.: 17/080,291

(22) Filed: Oct. 26, 2020

(65) Prior Publication Data

US 2021/0053015 A1 Feb. 25, 2021

Related U.S. Application Data

(63) Continuation-in-part of application No. PCT/US2019/029337, filed on Apr. 26, 2019.
(Continued)

(51) Int. Cl.
*B01D 67/00* (2006.01)
*B01D 53/22* (2006.01)
(Continued)

(52) U.S. Cl.
CPC ....... *B01D 67/0079* (2013.01); *B01D 53/228* (2013.01); *B01D 63/023* (2013.01);
(Continued)

(58) Field of Classification Search
None
See application file for complete search history.

(56) References Cited

U.S. PATENT DOCUMENTS

| | | | |
|---|---|---|---|
| 2018/0304193 A1* | 10/2018 | Al-Maythalony | B01D 71/64 |
| 2019/0247804 A1* | 8/2019 | Long | B01D 71/64 |
| 2020/0276542 A1* | 9/2020 | Chu | B01D 53/228 |

OTHER PUBLICATIONS

Tsuruoka, Takaaki et al., "Interfacial Synthetic Approach for Constructing Metal-Organic Framework Crystals Using Metal Ion-Doped Polymer Substrate", Crystal Growth and Design, 2016, 16, pp. 2472-2476. (Year: 2016).*

* cited by examiner

*Primary Examiner* — Jason M Greene
(74) *Attorney, Agent, or Firm* — Benjamin Aaron Adler

(57) ABSTRACT

Provided herein are in situ methods for fabricating a mixed-matrix membrane or a mixed-matrix hollow fiber membrane for increasing formation of zeolitic imidazolate framework nanoparticles inside the mixed-matrix membrane. Generally, in the method a polyimide polymer coated onto at least one support is hydrolzed with a base and the poly(amic acid)-salt film formed thereby undergoes ion exchange with a metal ion, treatment of the formed poly(amic acid)-metal salt film with an organic linker to produce metal-organic framework nanoparticles in situ, and imidization of the treated poly(amic acid)-metal salt film produces a polyimide/metal-organic framework mixed-matrix membrane or a mixed-matrix hollow fiber membrane module. Also provided is the mixed-matrix membrane and the polymer mixed-matrix hollow fiber membrane module fabricated by the methods and methods for separating a binary gas mixture via the fabricated mixed-matrix membrane.

25 Claims, 25 Drawing Sheets

Related U.S. Application Data

(60) Provisional application No. 62/663,200, filed on Apr. 26, 2018.

(51) Int. Cl.
*B01D 63/02* (2006.01)
*B01D 71/02* (2006.01)
*B01D 71/64* (2006.01)
*B01D 69/14* (2006.01)

(52) U.S. Cl.
CPC .......... *B01D 71/028* (2013.01); *B01D 71/64* (2013.01); *B01D 69/148* (2013.01); *B01D 2323/36* (2013.01); *B01D 2323/40* (2013.01)

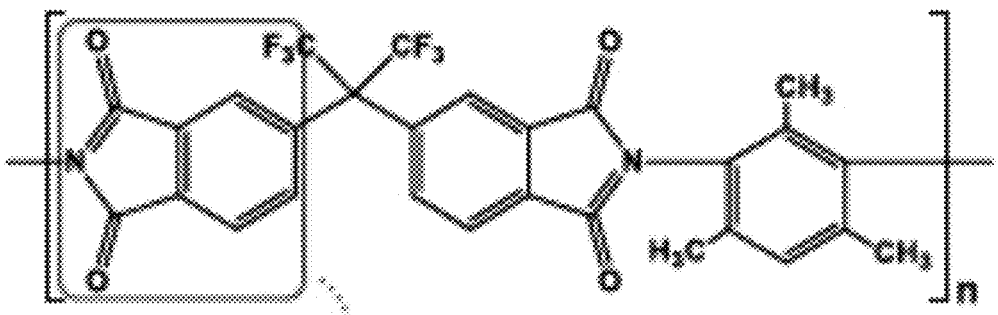
FIG. 1A
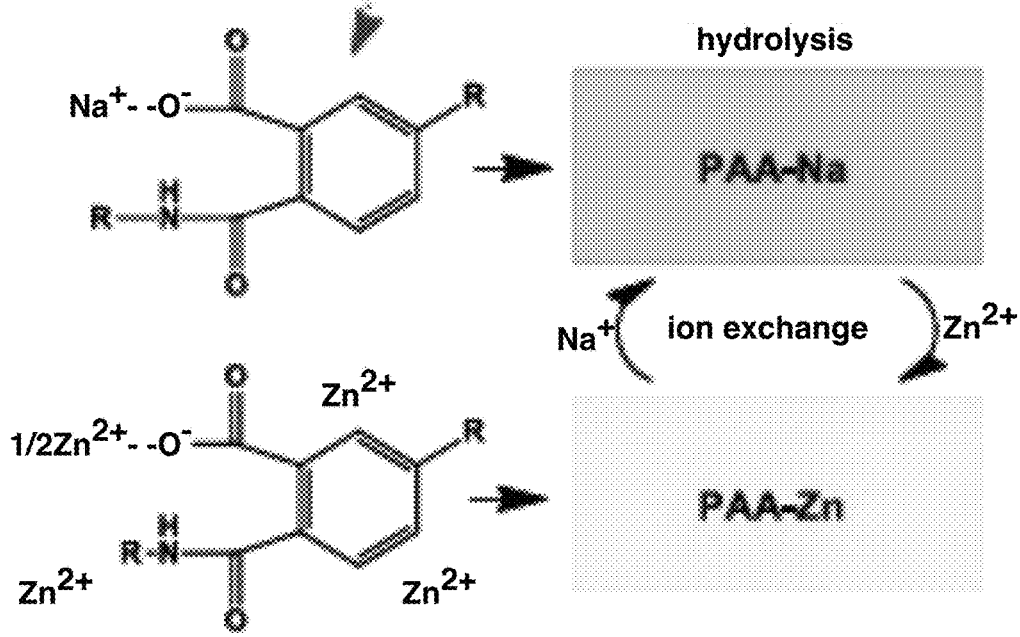
FIG. 1B
FIG. 1C
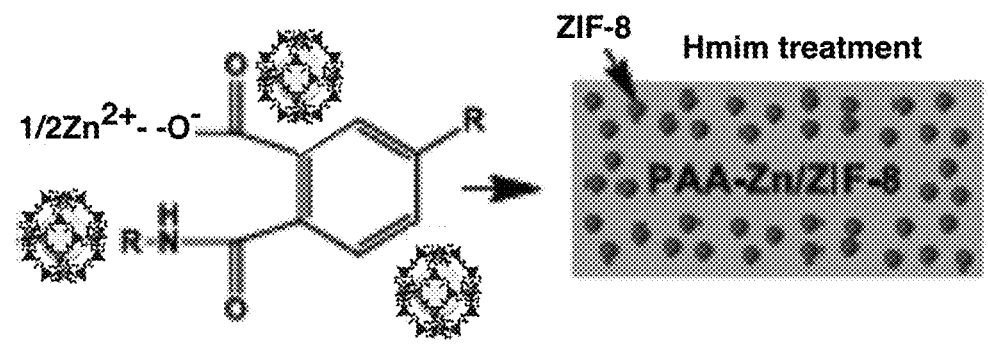
FIG. 1D
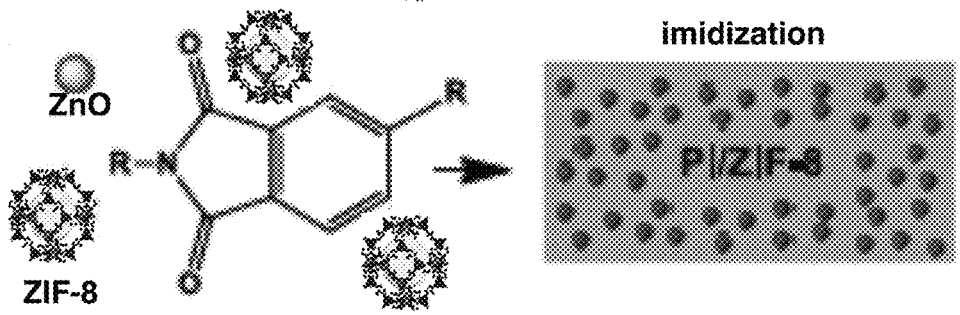
FIG. 1E

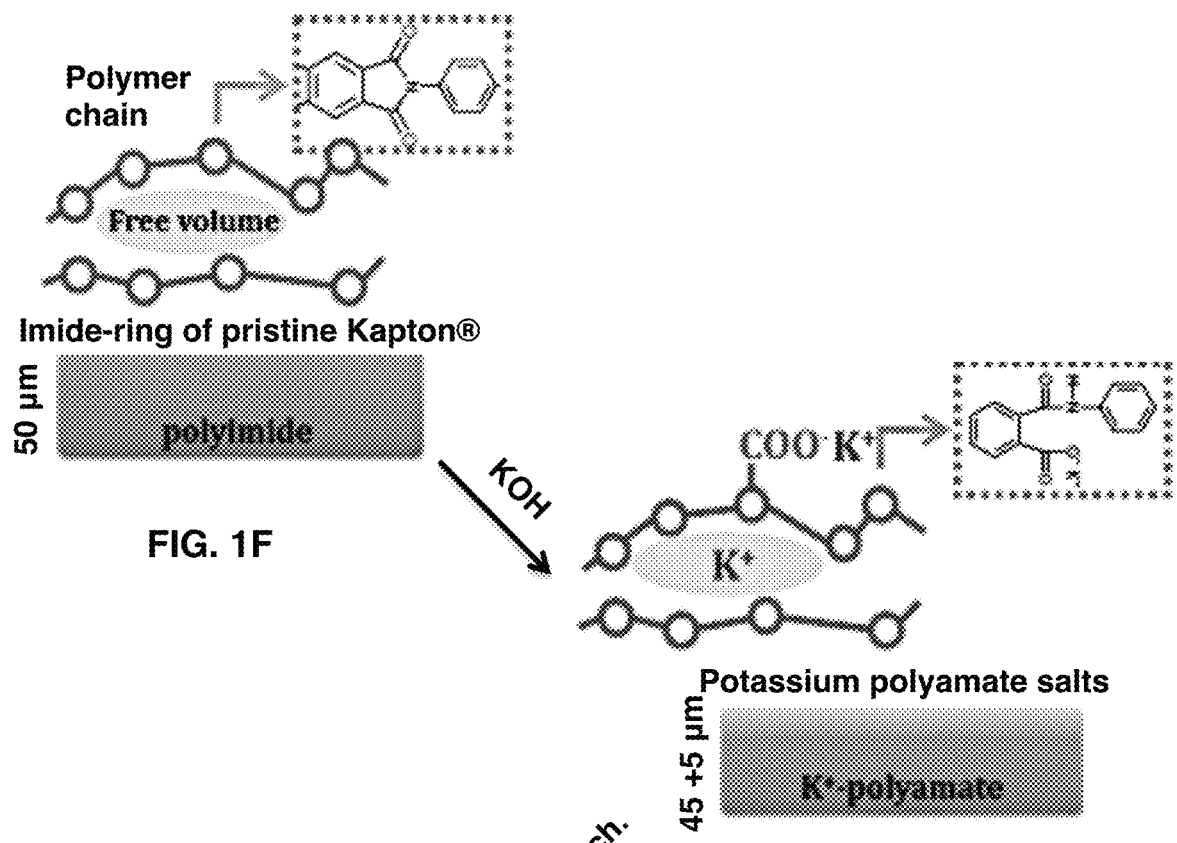
FIG. 1F
FIG. 1G
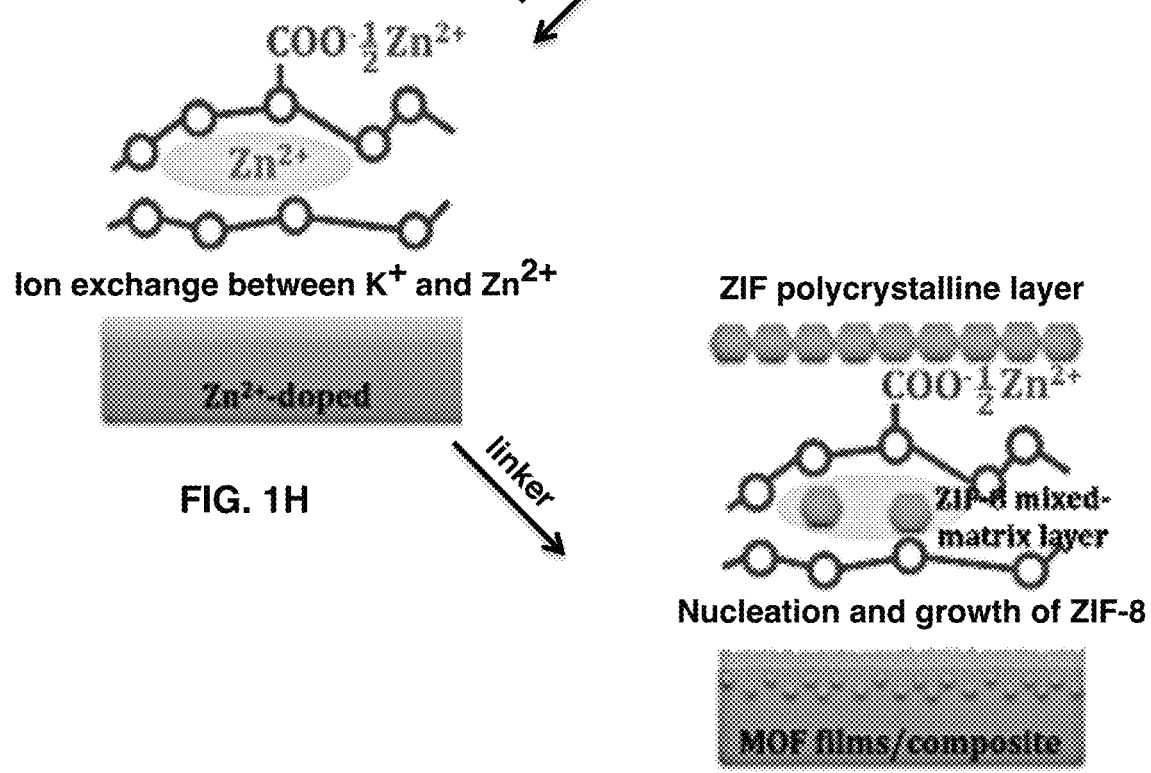
FIG. 1H
FIG. 1I

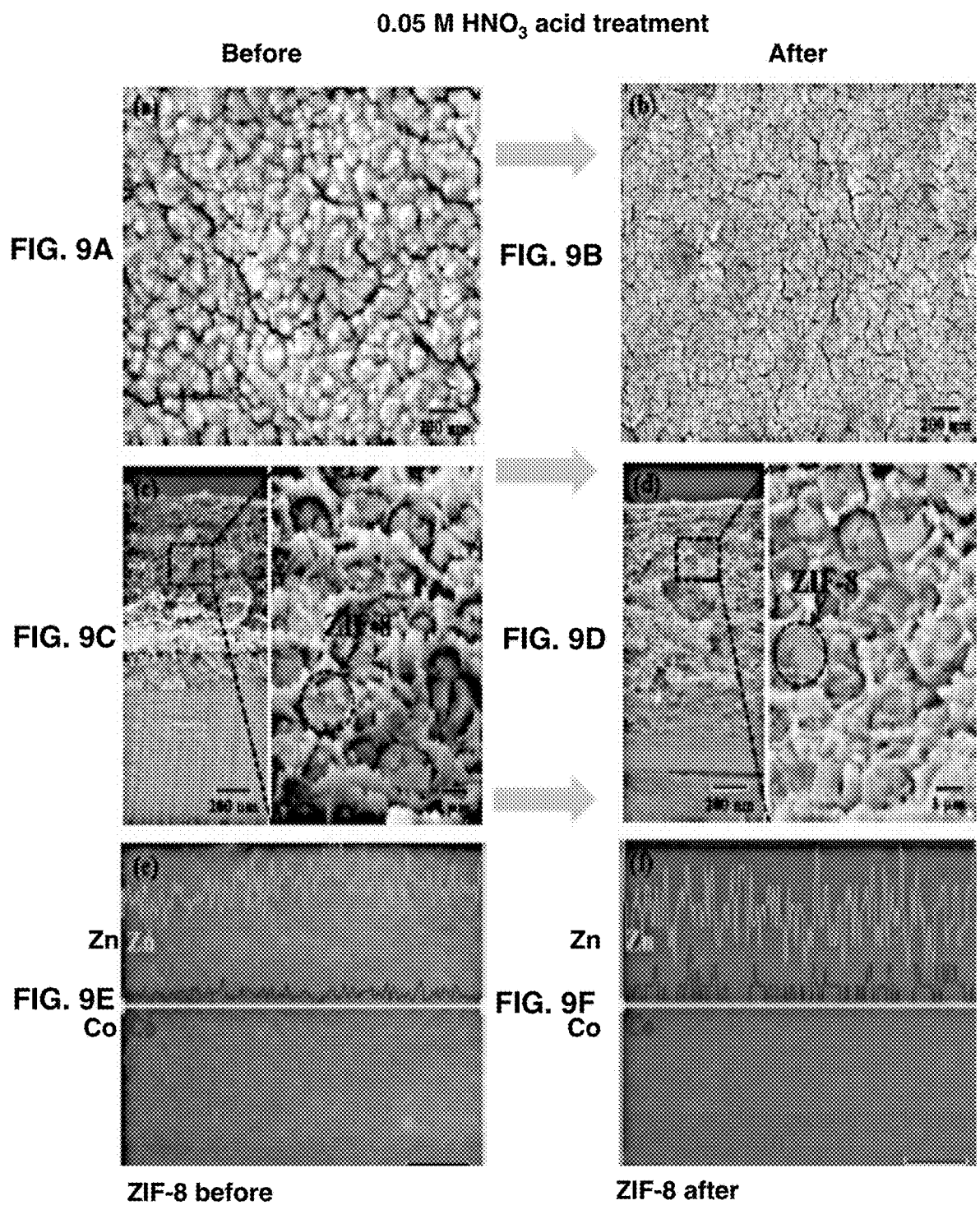

FIG. 11C
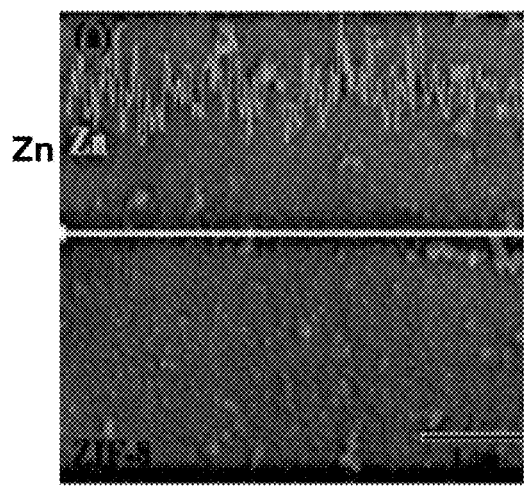
Zn
FIG. 11D
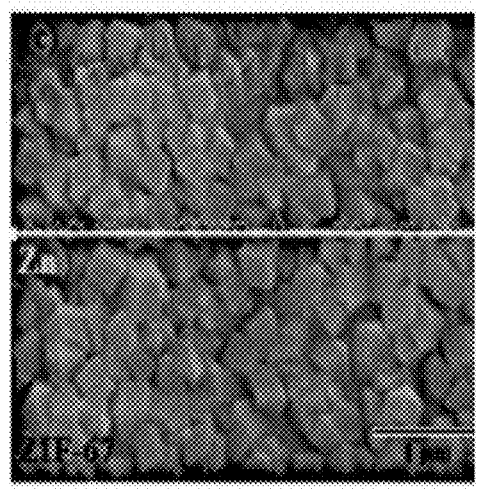
Zn
Zn/Co
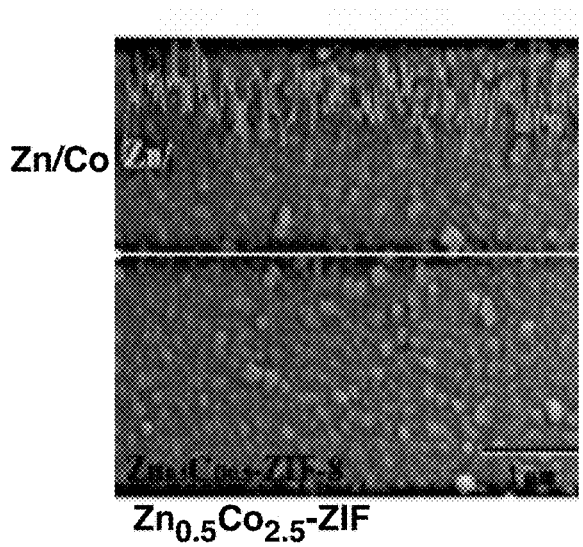
$Zn_{0.5}Co_{2.5}$-ZIF
FIG. 11E
Zn/Co
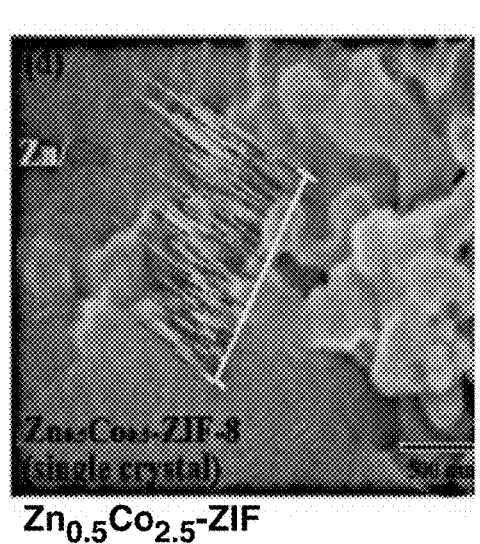
$Zn_{0.5}Co_{2.5}$-ZIF
(single crystal)
FIG. 11F

FIG. 11G    FIG. 11I    FIG. 11K
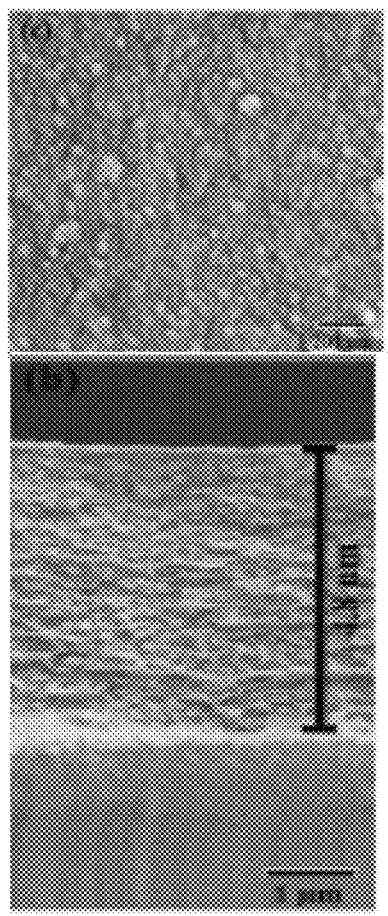 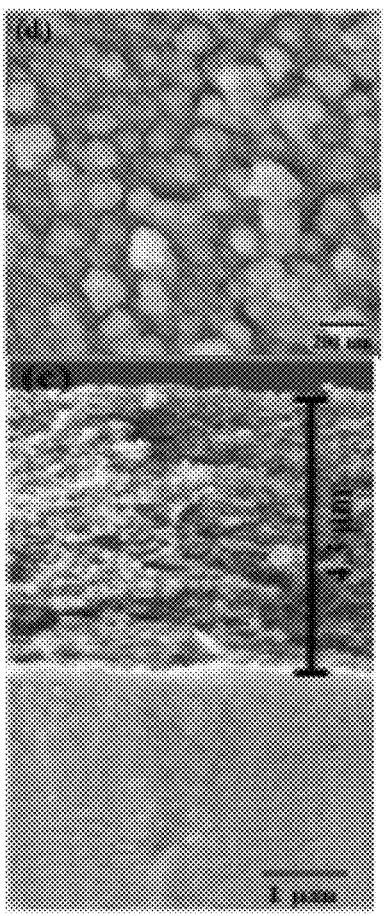 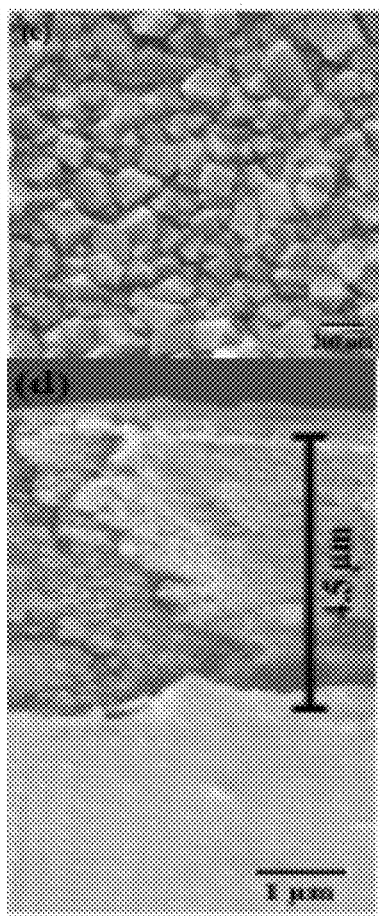
FIG. 11H    FIG. 11J    FIG. 11L
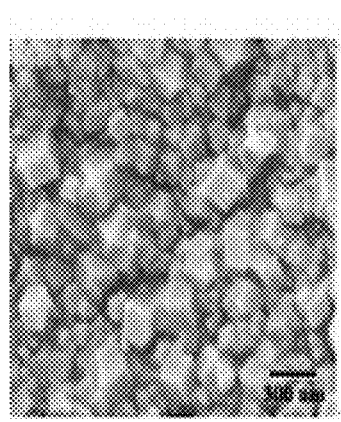 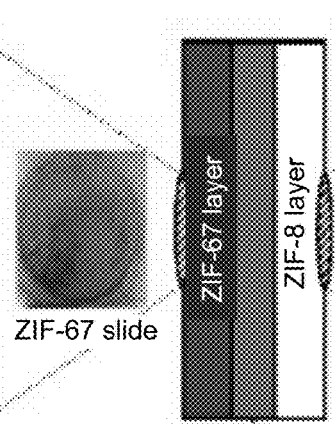 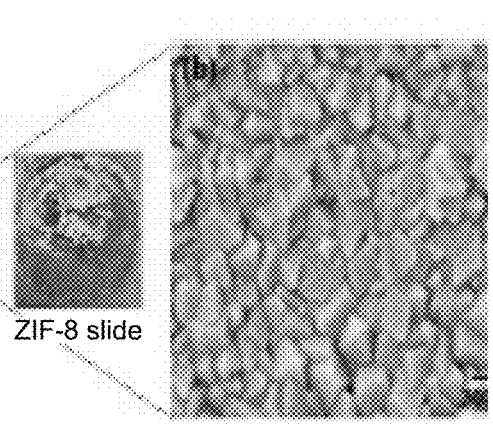
FIG. 11M

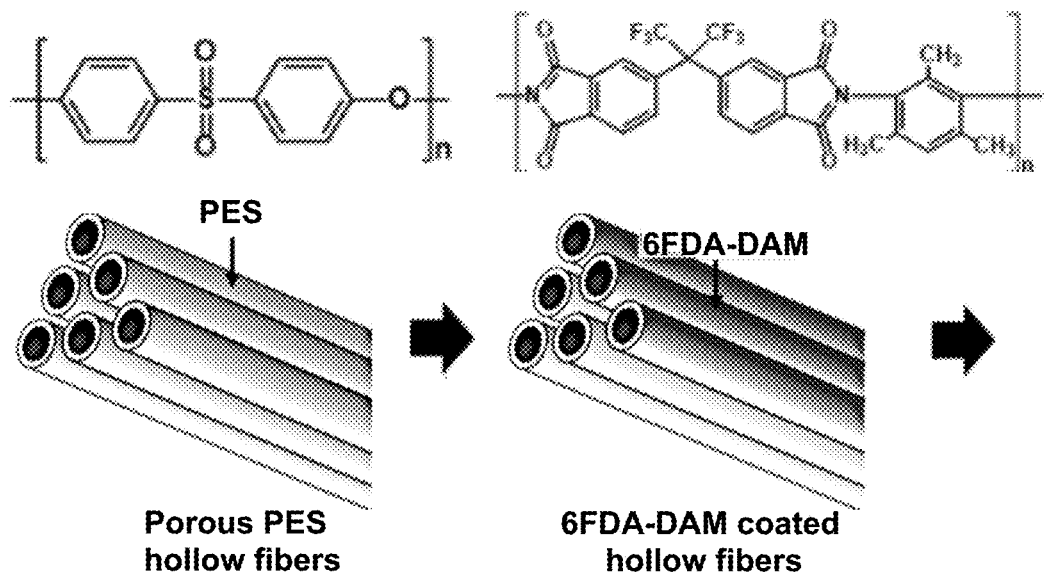
FIG. 17A  Porous PES hollow fibers
FIG. 17B  6FDA-DAM coated hollow fibers
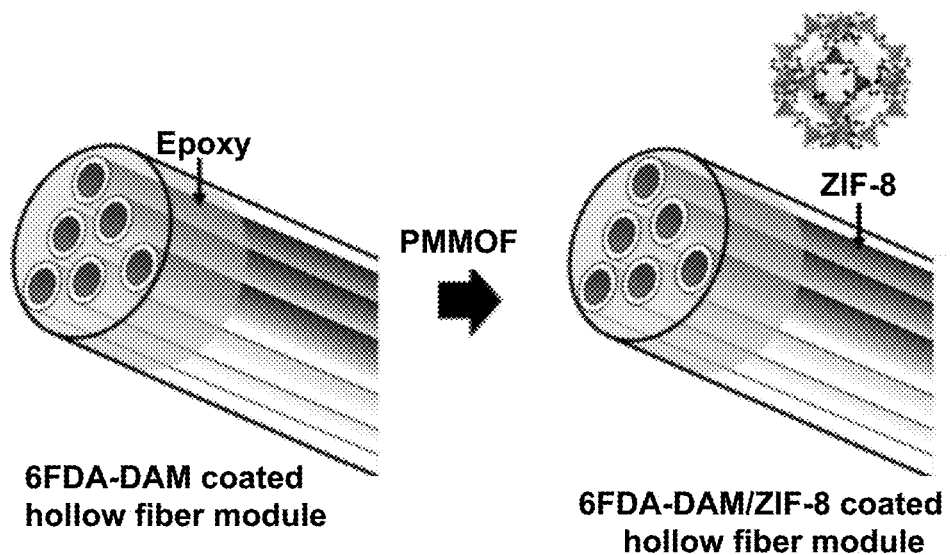
FIG. 17C  6FDA-DAM coated hollow fiber module
FIG. 17D  6FDA-DAM/ZIF-8 coated hollow fiber module

IN SITU FABRICATION OF METAL-ORGANIC FRAMEWORK FILMS AND MIXED-MATRIX MEMBRANES

CROSS-REFERENCE TO RELATED APPLICATION

This application is a continuation-in-part under 35 U.S.C. § 120 of international application PCT/US2019/029337, filed Apr. 26, 2019, which claims benefit of priority under 35 U.S.C. § 119(e) of provisional application U.S. Ser. No. 62/663,200, filed Apr. 26, 2018, the entirety of both of which is hereby incorporated by reference.

FEDERAL FUNDING LEGEND

This invention was made with support under Grant Numbers CBET-1510530 and DBI-0116835 awarded by the National Science Foundation. The government has certain rights in the invention.

BACKGROUND OF THE INVENTION

Field of the Invention

The present invention relates to the fields of metal-organic framework (MOF) thin films and mixed-matrix membranes. More specifically, the present invention relates to a membrane fabrication process for zeolitic-imidazolate framework thin films on polymers, i.e., polymer-supported zeolitic-imidazolate framework membranes) or ZIF/polymer composites, i.e., ZIF-containing mixed-matrix membranes).

Description of the Related Art

Metal-organic frameworks with unique properties have drawn considerable attention for a variety of advanced applications including gas storage, separation, sensing, and catalysis. Zeolitic-imidazolate frameworks (ZIFs), a subclass of MOFs, are one of the most widely studied metal-organic frameworks because of their permanent ultramicroporosities (<5.0 Å), tunable pores and chemical functionalities, and excellent chemical/thermal stabilities relative to other metal-organic frameworks. ZIFs are typically constructed by linking divalent metal ions (e.g., $Zn^{2+}$ and $Co^{2+}$) with imidazolate-based linkers, forming open structures analogous to those of zeolites. While ZIF materials are readily applicable in bulk/powder forms as adsorbents and catalysts, advanced applications including film-based sensors and membrane-based separations demand them to be fabricated as defect-free thin films typically supported on substrates or composites with other materials.

One method to fabricate metal-organic framework thin films was based on the interfacial reaction approach using metal-doped polymer substrates. Although the interfacial growth approach on modified polymer substrates is a versatile strategy for the construction on metal-organic framework films, there are, however, no reports on successful fabrication of ZIF thin films on polymer substrates using a similar approach. In addition, the current interfacial growth approach resulted only in the formation of metal-organic framework films on polymer substrate surfaces. It is often desirable to form metal-organic framework crystals inside polymer substrates (i.e., mixed-matrix composite films).

Membrane-based gas separation has attracted tremendous research interests as an energy efficient alternative to energy intensive conventional gas separation technologies such as cryogenic distillation. Propylene/propane separation, (1) in particular, is one of the most challenging separations (2) due to the very similar physical and chemical properties of the two gas molecules. Polycrystalline molecular sieve membranes such as ZIF-8 membranes showed high propylene/propane separation performances (3-4). Nevertheless, there have been no polycrystalline molecular sieve gas separation membranes commercialized due to their prohibitively high cost stemming mainly from difficulty of large scale fabrication (5). As such, mixed-matrix membranes (MMMs) combining the advantages of polymer membranes and inorganic molecular sieve membranes by incorporating inorganic molecular sieve particles within a polymer matrix have been intensively investigated for the past two decades (6-7).

Koros et al. (8) successfully demonstrated the first propylene-selective 6FDA-DAM/ZIF-8 hollow fiber mixed-matrix membranes (HFMMMs) with 30 wt % of ZIF-8 loading which to date seems to be the only HFMMM that showed improved propylene/propane separation. Tsuruoka et al. (9) reported growing MOF layers supported on polymer substrates based on an ion-doping strategy by hydrolyzing KAPTON polyimide (poly-oxydiphenylene-pyromellitimide) films with KOH and doping the hydrolyzed films with Al ions via ion exchange. MIL-53 layers were formed on the modified polymer substrates upon treating the ion-exchanged polymer substrates in a ligand solution under microwave irradiation. Marti et al. (10) reported the first in situ grown U10-66 containing mixed-matrix membranes by dissolving a polymer and a metal-organic framework precursor together followed by thermal curing. However, the membranes showed significant particle agglomeration and their gas separation performance was no better than those of conventionally prepared mixed-matrix membranes. This approach is not as general and more importantly not compatible with current polymer processing technologies.

Thus, there is a recognized need in the art for improved mixed-matrix membrane fabrication methods and processes. Specifically, the prior art is deficient in fabrication methods for the in situ formation of ZIF films or nanoparticles in polyimide-based polymer matrices. The present invention fulfills this longstanding need and desire in the art.

SUMMARY OF THE INVENTION

The present invention is directed to an in situ method for fabricating a mixed-matrix membrane. In this method, a polyimide polymer is coated onto at least one support and the polyimide polymer is hydrolyzed with a base to produce a poly(amic acid)-salt film. The salt ions in the poly(amic acid)-salt film are exchanged with metal ions in an aqueous metal salt solution to produce a poly(amic acid)-metal salt film. The poly(amic acid)-metal salt film is treated with an organic linker to produce metal-organic framework nanoparticles in situ and the treated poly(amic acid)-metal salt film is imidized to produce a polyimide/metal-organic framework mixed-matrix membrane.

The present invention is directed to a related in situ method for fabricating a mixed matrix membrane. In this method, the support is a plurality of hollow fiber membranes. The coating step comprises coating a layer of the polyimide polymer onto each of the plurality of hollow fiber membranes to produce a plurality of polyimide polymer hollow fiber membranes and assembling the plurality of polyimide polymer hollow fiber membranes into a module. The hydrolyzing, exchanging, treating, and imidizing steps follow as described herein.

The present invention also is directed to a mixed-matrix membrane hollow fiber module fabricated by the in situ method described immediately supra.

The present invention is directed further to a method for separating a propylene/propane gas mixture. In the method the propylene/propane gas mixture is flowed through the mixed-matrix membrane hollow fiber module described herein.

The present invention is directed further still to another related in situ method for fabricating a zinc-doped mixed-matrix membrane. In the method a polyimide polymer film is coated onto a support and the polyimide polymer is deimidized with a sodium-containing base to produce a poly(amic acid)-sodium salt (PAA-Na) film. Sodium salt ions in the PAA-Na film are exchanged with zinc ions to produce a poly(amic acid)-zinc salt (PAA-Zn) film. The PAA-Zn film is treated solvothermally with an organic linker to form zeolitic imidazolate framework nanoparticles in situ and the treated PAA-Zn film is re-imidized thermally to produce a polyimide/ZIF mixed-matrix membrane.

The present invention is directed further still to a mixed-matrix membrane fabricated by the in situ methods described herein.

The present invention is directed further still to a method for separating a binary gas mixture. In the method the binary gas mixture is flowed through the mixed-matrix membranes described herein.

The present invention is directed further still to a method for increasing formation of zeolitic imidazolate framework nanoparticles inside a mixed-matrix membrane. In the method imide rings in a polyimide polymer are opened in the presence of a hydrolyzing sodium-containing base to enlarge a free volume of the polyimide polymer and to increase the hydrophilicity thereof. Salt ions formed in the hydrolyzed polymer are exchanged with metal ions in an aqueous salt solution to form a metal-doped polymer film where the enlarged free volume and increased hydrophilicity enable increased diffusion of the metal ions into the hydrolyzed polymer. Imidazolate framework nanoparticles are formed inside the metal-doped polymer film in the presence of an organic linker and the opened imide rings in the hydrolyzed polymer are re-imidized to produce a polyimide/ZIF mixed-matrix membrane.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 1A-1I presents a schematic of the PMMOF process using 6FDA-DAM (FIGS. 1A-1E) and KAPTON (KAP) polyimides (FIGS. 1F-1I). For 6FDA-DAM the steps show a pristine polyimide (PI) (FIG. 1A), hydrolysis to a poly (amic acid) sodium salt (PAA-Na) (FIG. 1B), zinc-ion exchange to a poly(amic acid) zinc salt (PAA-Zn) (FIG. 1C), Hmim treatment to a poly(amic acid) zinc salt with ZIF-8 (PAA-Zn/ZIF-8) (FIG. 1D), and imidization to polyimide with ZIF-8 (PI/ZIF-8) (FIG. 1E). For KAPTON the steps show a pristine KAP (FIG. 1F), hydrolysis with KOH to the K+-KAP polyamate (FIG. 1G), zinc-ion exchange to the Zn2+-doped KAP zinc salt (FIG. 1H), and treatment with Hmim linker to form MOF films/composite (FIG. 1I).

FIG. 2A are XRD patterns of PMMOF processed MATRIMID and 6FDA-DAM polyimides. * indicates peaks for α-alumina support. FIG. 2B is ATR-IR spectra of samples at each PMMOF step (hydrolysis time is 5 h). The overlapped dotted lines are the 6FDA-DAM spectra for comparison. FIG. 2C shows the degree of deimidization of PAA-Zn/ZIF-8 with different hydrolysis times. FIG. 2D is the ATR-IR spectra of PI, PAA-Na, PI treated in a zinc solution (PI-Zn), and PI treated in an Hmim solution (PI-Hmim). FIGS. 2E-2G are cross-sectional SEM images of pristine and PMMOF processed 6FDA-DAM samples of PI (FIG. 2E), PUZIF-8 hydrolyzed for 5 h (FIG. 2F) and 8 h (FIG. 2G)

FIG. 3A is a wide scan XPS spectra, FIG. 3B is a narrow-scan XPS spectra of PAA-Na for Na 1s, FIG. 3C is a Zn 2p3/2 XPS spectra and curve fits of unwashed PAA-n (left) and washed (right). FIG. 3D are XRD patterns of PUZIF-8. * indicates peaks for α-alumina support.

FIG. 4A shows XRD patterns of PUZIF-8 before and after dissolving PI in NMP. FIGS. 4B-4C are SEM images of a top view and cross-sectional view, respectively, of PUZIF-8. FIGS. 4D-4E are SEM images of a top view and cross-sectional view, respectively, of surface acid treated PUZIF-8. FIG. 4F shows XRD patterns of PI/ZIF-8 with and without surface acid treatment. * indicates peaks for α-alumina support.

FIG. 6A is spectra of a pristine KAP film and KAP films subjected to different hydrolysis times of 2 (KAP-2), 4 (KAP-4), 6 (KAP-6), 8 (KAP-8), and 10 (KAP-10) minutes. FIG. 6B shows the relative (110) intensity of KAP-x-Zn-ZIF-8 with respect to that of KAP-2-Zn-ZIF-8. FIG. 6C illustrates the linearity of the relative (110) intensity of the KAP films in FIG. 6B. FIG. 6D compares the relative intensities of ZIF-8 simulation, KAP-0-Zn-ZIF-8 and KAP-6-Zn-ZIF-8.

FIG. 7H shows the changes in ZIF-8/polymer composite layer thickness of KAP-x-Zn-ZIF-8 with respect to KOH treatment time.

FIGS. 9A-9F show top and cross-sectional SEM images (FIGS. 9A-9D) and EDX line scan analyses (FIGS. 9E-9F) of ZIF-8 film surfaces before and after acid treatment.

FIGS. 11A-11M show PXRD patterns, ATR-FTIR spectra, EDX line scans analysis and top and cross-sectional SEM images of ZIF-8, $Zn_{0.5}Co_{0.5}$-ZIF-8 and ZIF-67. FIG. 11A shows the PXRD patterns of the ZIF films and FIG. 11B is an ATR-FTIR spectra showing metal-to-nitrogen stretching vibration of the ZIF thin films. FIGS. 11C-11F are EDX line scan analyses on a ZIF-8 film (FIG. 11C), a co-doped $Zn_{0.5}Co_{0.5}$-ZIF-8 film surface (FIG. 11D), a ZIF-67 thin film on polymer substrate (FIG. 11E), and a $Zn_{0.5}Co_{0.5}$-ZIF-8 single crystal (FIG. 11F). FIGS. 11G-11L are top and cross-sectional SEM images, respectively of ZIF-8 (FIGS. 11G-11H), $Zn_{0.5}$—$Co_{0.5}$-ZIF (FIGS. 11I-11J), ZIF-67 (FIGS. 11K-11L) and FIG. 11M is a top SEM image of a Janus film with a ZIF-67 layer on one side and a ZIF-8 layer on the other side.

FIGS. 12A-12B are XRD patterns after methanol-based (FIG. 12A) and ethanol-based (FIG. 12B) treatment. FIG. 12C shows the normalized crystal peak intensity changes of the (110) plane of PI/ZIF-8 films and FIG. 12D shows the relative (110) peak intensity of PI/ZIF-8 after the surface acid treatment normalized by that before the surface acid treatment.

FIG. 15A is a $C_3H_6$ permeability versus $C_3H_6/C_3H_8$ separation factor plot with the $C_3H_6/C_3H_8$ upper bond curve (11). The solid circles are the experimental data of PMMOF processed mixed-matrix membranes and the open circles are the literature data for conventional molecular sieve blending based mixed-matrix membranes (12). The arrows direct the increase of ZIF-8 concentration and the annotated percentage is the volume percentage of ZIF-8 in mixed-matrix membranes. FIG. 15B shows the $C_3H_6/C_3H_8$ separation of PMMOF processed mixed-matrix membranes, ideal mixed-matrix membranes and predicted polymers based on PMMOF processed mixed-matrix membranes with the upper bound curve (3). The same color represents the same zinc concentration; red-zinc 8 mmol, orange-zinc 16 mmol, green-zinc 24 mmol, cyan-zinc 32 mmol, and blue-zinc 40 mmol.

FIG. 16A are photographs of ZIF-8 (top), ZIF-67 (center) and HKUST-1 (bottom). FIG. 16B are XRD patterns of PI/ZIF-8 (top), PI/ZIF-67 (center) and PI/HKUST-1 (bottom). * indicates peaks for α-alumina support and the y-axis is the intensity in arbitrary units (a.u.).

FIGS. 17A-17D is a schematic illustration of the evolution of commercial polymer (PES) HFMs (FIG. 17A) to PI-coated polymer HFMs FIG. 17B) to a PI-coated HFM module FIG. 17C) to a PI/ZIF-8 MMHFM module FIG. 17D).

DETAILED DESCRIPTION OF THE INVENTION

Figure 2A:
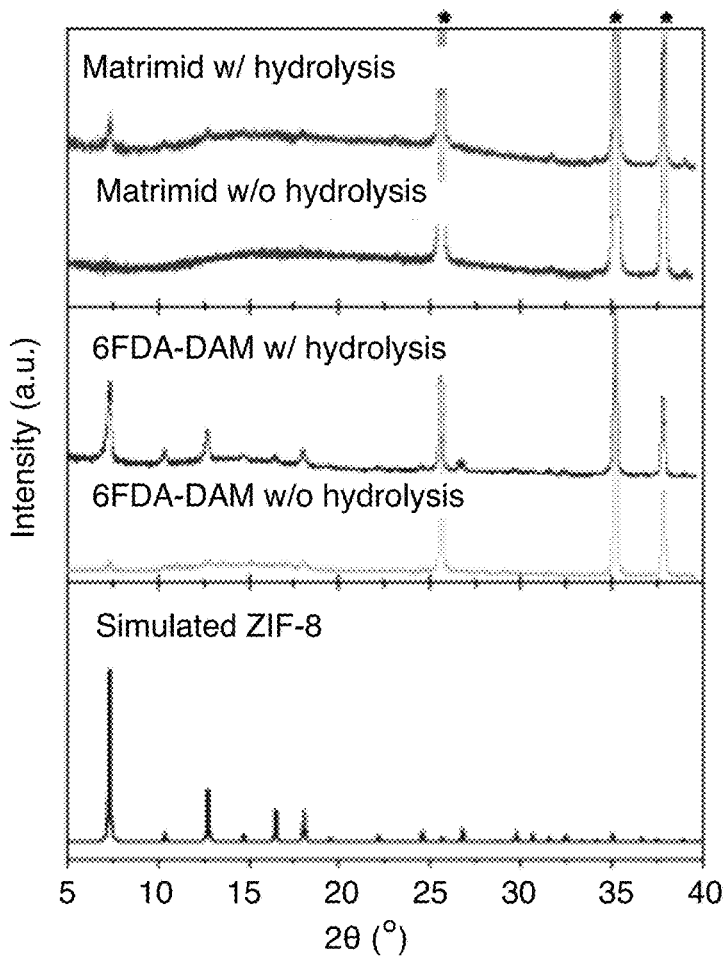
FIGS. 2A-2G show XRD patterns, ATR-IR spectra and cross-sectional SEM images of pristine and PMMOF processed polyimides.

For convenience, before further description of the present invention, certain terms employed in the specification, examples and appended claims are collected herein. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, components, method steps, and/or methods of the invention. It is contemplated that any composition, component or method described herein can be implemented with respect to any other composition, component or method described herein.

The term "or" in the claims refers to "and/or" unless explicitly indicated to refer to alternatives only or the alternatives are mutually exclusive, although the disclosure supports a definition that refers to only alternatives and "and/or".

The terms "comprise" and "comprising" are used in the inclusive, open sense, meaning that additional elements may be included.

The term "including" is used herein to mean "including, but not limited to", "Including" and "including but not limited to" are used interchangeably.

The term "about" is used herein to refer to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

In one embodiment of the present invention, there is provided an in situ method for fabricating a mixed-matrix membrane, comprising coating a polyimide polymer film onto at least one support; hydrolyzing the polyimide polymer with a base to produce a poly(amic acid)-salt film; exchanging salt ions in the poly(amic acid)-salt film with metal ions in an aqueous metal salt solution to produce a poly(amic acid)-metal salt film; treating the poly(amic acid)-metal salt film with an organic linker to produce metal-organic framework nanoparticles in situ; and imidizing the treated poly(amic acid)-metal salt film to produce a polyimide/metal-organic framework mixed-matrix membrane.

In this embodiment the polyimide polymer may be (4,4-(Hexafluoroisopropylidene)diphthalic anhydride-2,4,6-trimethyl-1,3-phenylene diamine (6FDA-DAM), pyromellitic dianhydrides oxidianiline (PMDA-ODA) or 3,3-4,4-benzophenone tetracarboxylic dianhydride diaminophenylindane (BTDA-DAPI). Also in this embodiment the support may be a hollow fiber or a hollow fiber membrane, a fiber, a flat sheet, or a film. In addition the base may be sodium formate, sodium hydroxide, potassium hydroxide, barium hydroxide, cesium hydroxide, strontium hydroxide, calcium hydroxide, lithium hydroxide, or rubidium hydroxide.

In this embodiment the aqueous metal salt solution may be a nitrate, acetate, sulfate or chloride salt solution of zinc, cobalt, magnesium, manganese, iron, nickel, copper, or cadmium or a combination thereof. Also, the organic linker may be imidazole, 2-methylimidazole, 2-ethylimidazole, 2-nitroimidazole, benzimidazole, 6-nitrobenzimidazole, or purine. Particularly, the organic linker may be 2-methylimidazole.

In an aspect of this embodiment the hydrolyzing step opens imide rings in the polyimide polymer to produce a poly(amic acid) sodium salt. Particularly, the hydrolyzed polyimide polymer has an increase in free volume and hydrophilicity such that diffusion of the zinc ions inside the polymer is increased. Further to this aspect the exchanging step exchanges sodium ions in the poly(amic acid) sodium salt with zinc ions to form a poly(amic acid) zinc salt film. Further still to these aspects the treating step produces zeolitic imidazolate framework nanoparticles inside the poly(amic acid) zinc salt film to form a poly(amic acid)-Zn/zeolitic imidazolate framework. Particularly, the zeolitic imidazolate framework is ZIF-8 or ZIF-67. Further still to these aspects the imidizing step produces a polyimide/zeolitic imidazolate framework mixed-matrix membrane. Particularly, the polyimide/zeolitic imidazolate framework mixed-matrix membrane is polyimide/ZIF-8.

In a related embodiment, the support may be a plurality of hollow fiber membranes, where the coating step comprises coating a layer of the polyimide polymer onto each of the plurality of hollow fiber membranes to produce a plurality of polyimide polymer hollow fiber membranes; and assembling the plurality of polyimide polymer hollow fiber membranes into a module.

Related to this embodiment there is provided a mixed-matrix membrane hollow fiber module fabricated by the method as described immediately supra. An example of the mixed-matrix membrane hollow fiber module is a 6FDA-DAM/ZIF-8 mixed-matrix hollow fiber membrane module.

Also related to these embodiments there is provided a method for separating a propylene/propane gas mixture, comprising flowing the propylene/propane gas mixture through the mixed-matrix membrane hollow fiber module fabricated as described supra.

In yet another related embodiment of the present invention, there is provided an in situ method for fabricating a zinc-doped mixed-matrix membrane, comprising coating a polyimide polymer film onto a support; deimidizing the polyimide polymer with a sodium-containing base to produce a poly(amic acid)-sodium salt (PAA-Na) film; exchanging sodium salt ions in the PAA-Na film with zinc ions to produce a poly(amic acid)-zinc salt (PAA-Zn) film; treating, solvothermally, the PAA-ZN film with an organic linker to form zeolitic imidazolate framework (ZIF) nanoparticles in situ; and re-imidizing, thermally, the treated PAA-ZN film to produce a polyimide/ZIF mixed-matrix membrane.

In this related embodiment the polyimide polymer and the support may be as described supra. Also, the base may be sodium formate or sodium hydroxide. In addition the organic linker may be 2-methylimidazole (Hmim). Furthermore, the polyimide/ZIF mixed-matrix membrane is ZIF-8. In one aspect of this related embodiment the deimidizing step may comprise hydrolyzing the polyimide polymer with sodium formate or sodium hydroxide. In another aspect the exchanging step may comprise immersing the PAA-Na into an aqueous nitrate, acetate, sulfate or chloride salt solution of zinc. In yet another aspect treating step may comprise treating the PAA-ZN film with 2-methylimidazole (Hmim).

In yet another embodiment of the present invention there is provided a mixed-matrix membrane fabricated by the methods as described supra. In one aspect of this embodiment the mixed-matrix membrane may be doped with at least one of zinc, cobalt, magnesium, manganese, iron, nickel, copper, or cadmium. Particularly, the mixed-matrix membrane may be doped with zinc or cobalt. Representative examples of this membrane is a polyimide/ZIF-8 membrane doped with zinc or a polyimide/ZIF-67 membrane doped with cobalt. In another aspect of this embodiment the mixed-matrix membrane may be fabricated from each of a plurality of polymer hollow fiber membranes comprising a module. An example of this membrane is a 6FDA-DAM/ZIF-8 mixed-matrix hollow fiber membrane.

In this embodiment and aspects thereof the mixed-matrix membrane may have a structure with a permeability and a separation factor that enables separation of gases in a binary mixture. An example of the gases in the binary mixture are propylene gas and propane gas.

In yet another embodiment of the present invention there is provided a method for separating a binary gas mixture, comprising flowing the binary gas mixture through the mixed-matrix membrane as described supra. In this embodiment the binary gas mixture may be a propylene/propane gas mixture.

In yet another embodiment of the present invention there is provided a method for increasing formation of zeolitic imidazolate framework nanoparticles inside a mixed-matrix membrane, comprising opening imide rings in a polyimide polymer in the presence of a hydrolyzing sodium-containing base to enlarge a free volume of the polyimide polymer and to increase the hydrophilicity thereof; exchanging sodium salt ions formed in the hydrolyzed polymer with metal ions in an aqueous salt solution to form a metal-doped hydrolyzed polymer film, whereby the enlarged free volume and increased hydrophilicity enable increased diffusion of the metal ions into the polymer; forming zeolitic imidazolate framework nanoparticles inside the metal-doped polymer film in the presence of an organic linker; and re-imidizing the opened imide rings in the hydrolyzed polymer to produce a polyimide/ZIF mixed-matrix membrane.

In this embodiment the polyimide polymer, the sodium containing base and the organic linker may be as described supra. Also in this embodiment the polyimide polymer may be coated onto a hollow fiber, a fiber or a flat sheet. In addition, the aqueous salt solution may be a nitrate, acetate, sulfate or chloride salt solution containing metal ions of zinc, cobalt, magnesium, manganese, iron, nickel, copper, or cadmium or a combination thereof. Furthermore, the polyimide/ZIF mixed-matrix membrane may be ZIF-8 or ZIF-67.

Provided herein is a mixed-matrix membranes (MMMs) fabrication process by in situ growing of continuous metal-organic framework thin films on a polymer substrate surface with formation of particles, such as nanoparticles, inside the polymer matrix and the mixed-matrix membranes so formed. The process is polymer-modification-enabled in situ metal-organic framework formation (PMMOF). The polymer may be a polyimide and the polymer substrate may be an ion-exchanged polymer substrate with various geometries. The metal-organic framework may be a zeolitic-imidazolate-framework such as, but not limited to ZIF-8 or ZIF-67.

Generally, in the PMMOF process to fabricate a mixed-matrix membrane, the first step, hydrolysis of the polyimide polymer, enlarges the polymer free volume and makes spaces in which to grow the ZIF nanoparticles, for example, but not limited to, ZIF-8 nanoparticles, by physically absorbed excessive zinc ion sources. For ZIF-8, the in situ grown nanoparticles were uniformly dispersed inside the polymers with its shape and size rod-like and less than ~100 nm. By varying the zinc concentration in an exchange solution, the ZIF-8 concentration increased up to 32.9 vol %. The thickness of the mixed-matrix layers is controllable by varying the kinetics of alkali hydrolysis. Thus, also provided is a method to increase the formation of ZIF nanoparticles within the mixed-matrix membrane utilizing the PMMOF process. The method utilizes the enlarged polymer free volume and resultant increase in hydrophilicity to enable more metal ions to diffuse within the enlarged polymer volume.

The PMMOF process also enables the transformation of a polymer hollow fiber membrane (HFM) module to a mixed-matrix hollow fiber membrane (MMHFM) module. This scales up the fabrication of the single mixed-matrix membranes. Generally, any polyimide may be coated on a hollow fiber membrane and subjected to the PMMOF process. Representative examples of a polymer HFM is 6FDA-DAM (4,4'-(hexafluoroisopropylidene) diphthalic anhydride-2,4,6-trimethyl-1,3-diaminobenzene), MATRIMID (diamine, 5(6)-amino-1-(4'-aminophenyl)-1,3,-trimethylind or TORLON (polyamide-imide) coated or layered on a commercially available hollow fiber membrane. Examples of a mixed-matrix hollow fiber membrane is, but not limited to, 6FDA-DAM/ZIF-8 MMHFM or 6FDA-DAM/ZIF-67 MMHFM.

Generally, the PMMOF process of hydrolysis, ion exchange, ligand treatment and imidization is applied to the polymer-coated hollow fiber membranes comprising the module. Prior to initiating the PMMOF process one to a plurality of the polymer coated hollow fiber membranes, for example, but not limited to, one to about seven polymer coated HFMs, may be assembled in the module. In this instance in applying PMMOF to the polymer HFM milder hydrolysis conditions are required due to a thinner polymer layer on the HFMs compared to that of the polymer film when preparing a single mixed-matrix membrane. The PMMOF fabrication of the mixed-matrix hollow fiber membrane module also requires a means to remove air bubbles during ion exchange, for example, evacuation under vacuum. Moreover, a means to prevent damage to the skin layers within the module during ligand treatment is required, for example, by maintaining a packing density of less than 30%

In addition, there is provided a method for propylene/propane separation which utilizes the mixed-matrix membranes fabricated by the PMMOF process. These mixed-matrix membranes demonstrate a significantly higher propylene/propane separation factor than that of conventionally prepared mixed-matrix membranes. This significant enhancement is attributed to better adhesion between the polymer and ZIF-8, better dispersion of ZIF-8 nanoparticles, and enhanced densification of polymer matrix by in situ grown ZIF-8. Alternatively, the dual gas separation my be performed utilizing the mixed-matrix hollow fiber membrane module, for example, the 6FDA-DAM/ZIF-8 MMHFM, with results equivalent to separation by a single fiber mixed-matrix membrane.

The PMMOF fabrication process is scalable and cost effective because:

a) PMMOF maintains the cost effective processing of the polymer which is approximately $20 for every 1 square meter of membrane area. Moreover, PMMOF has a low chemical consumption. Most of the chemicals used are aqueous based. Any polyimide or polymer containing an imide ring is suitable. Furthermore, the use of commercially available preformed polymer hollow fibers and modules significantly reduces the membrane cost.

(b) PMMOF is a quick in situ method. The synthesis of a polymer dense film or hollow fiber is decoupled from MMM synthesis. The process enables formation of high-quality membranes on commercially available, pre-packaged polymer hollow fiber modules.

(c) PMMOF is a straightforward scale-up process. PMMOF is compatible with existing membrane manufacturing processes because mixed-matrix membranes comprise a polymeric membrane having small nanoparticles embedded inside the polymer matrix.

The following examples are given for the purpose of illustrating various embodiments of the invention and are not meant to limit the present invention in any fashion.

Example 1

Methods and Materials for In Situ Formation of Zeolitic-Imidazole Framework Thin Films Materials KAPTON HN films (pyromellitic dianhydrides oxidianiline (PMDA-ODA) (50 μm thick, DuPont) and two commercial polyimide-based polymers, 6FDA-DAM (4,4-(Hexafluoroisopropylidene) diphthalic anhydride 2,4,6-trimethyl-1,3-phenylenediamine, Mw: 148 k, PDI: 2.14) and MATRIMID 5218 (3,3-4,4-benzophenone tetracarboxylic dianhydride diaminophenylindane, BTDA-DAPI) were used. 6FDA-DAM was purchased from Akron Polymer Systems Inc. while MATRIMID 5218 was generously provided by Huntsman Corp. To dissolve polymers, N,N-dimethylformamide (DMF) (C3H7NO, >99.8%, Alfa Aesar), tetrahydrofuran (THF) ($C_4H_8O$, >99%, Alfa Aesar), and N-methyl-2-pyrrolidone (NMP) ($C_5H_9NO$, ≥99%, Sigma-Aldrich) were used as solvents. For the PMMOF process, sodium formate (HCOONa, ≥99%), zinc nitrate hexahydrate ($Zn(NO_3)_2.6H_2O$, 98%), cobalt(II) nitrate hexahydrate ($Co(NO_3)_2.6H_2O$, 98%), copper(II) nitrate trihydrate ($Cu(NO_3)_2.3H_2O$, ≥99%), and 2-methylimidazole (Hmim) ($C_4H_6N_2$, 99%) were obtained from Sigma-Aldrich. As other reagents, 1,3,5-benzene tricarboxylic acid (H3BTC) ($C_9H_6O_6$, 98%, Alfa Aesar), methanol ($CH_3OH$, > 99.8%, Alfa Aesar), ethanol (C2H5OH, 94-96%, Alfa Aesar), and hexane ($C_6H_{14}$, ≥98.5%, VWR International) were used. All chemicals were used as-received without further purification.

Preparation of Porous Hollow Fibers and Flat Sheet

Porous MATRIMID R hollow fibers were fabricated by a dry-wet jet spinning process following a procedure previously optimized and reported in Woo et al. (13). Dope and bore solution compositions as well as spinning parameters were appropriately manipulated to obtain hollow fibers with porous morphology on both bore and shell side. Asymmetric MATRIMID R flat sheet substrates were prepared by the dry-wet phase inversion method (14). The polymer dope solutions were prepared by dissolving MATRIMID R powder (1.25 g, 25.0 wt %) in THF (0.86 g, 17.2 wt %) and DMF (2.59 g, 51.8 wt %) co-solvent mixture. The co-solvent of the volatile THF and the non-volatile DMF with 1:3 ratio was used to increase the local polymer concentration at the surface during the drying step, forming asymmetric structures. A nonsolvent, ethanol (0.30 g, 6.0 wt %) was added to the mixture to increase phase inversion rate. Mixing process was done at room temperature overnight. The dope solution was poured on a flat glass substrate and casted using a film casting knife with clearance of 346 μm. The volatile components were evaporated for 15 s in air. Then, the as-casted films were immediately immersed in water at 25° C. for 24 hrs. The films were solvent exchanged in ethanol for 30 min and then in hexane for 30 min. Finally, the films were dried at room temperature in air for 1 hr and further dried at 60° C. for 2 hrs.

Surface Modification and Metal Doping of Polymer Substrates

Modification and ion-exchange of KAPTON and MATRIMID films were performed following procedure reported by Tsuruoka et al. (21) with a slight adjustment. Pristine KAPTON and MATRIMID films with one side protected (2.5×2.5 $cm^2$) were treated in 5 M aqueous KOH solutions at 50° C. for different period of time, and then rinsed with copious amount of DI water. One side of the films was sealed with epoxy to ensure that the surface modification took place only on the exposed sides. Next, the films were immersed in 100 mM aqueous zinc nitrate hexahydrate solutions for 1 hr. The $Zn^{2+}$-doped films were then washed with copious amount of DI water. Excess metal solution and DI water on the polymer substrates were carefully removed using Kimwipes.

In Situ Solvothermal Formation of ZIF-8 Crystals on and Inside Polymer Substrates To form ZIF-8 crystals on and inside the polymer substrates, the Zn2+-doped polymer films were solvothermally treated in a linker solution based on a previous recipe (15) with a minor modification. Briefly, a linker precursor solution was prepared by dissolving 2.59 g of 2-methylimidazole (Hmlm) and 0.125 g of sodium formate in 30 ml of methanol (hereafter, linker solution). $Zn^{2+}$-doped polymer films were positioned vertically in a Teflon-lined autoclave containing the linker solution. The autoclave was kept in a convection oven at 120° C. for 2 hrs. After synthesis, the films were rinsed with methanol several times and washed with fresh methanol overnight.

Preparation of Polymer Films

Thin polymer films were coated on porous α-alumina supports (diameter of 2.2 cm) by using a solution casting method with the uniform thickness of 8.0±1.5 μm. Preparation of α-alumina supports is described elsewhere. 6 In a typical procedure for 6FDA-DAM films, 2 wt % of a polymer dope solution was prepared by dissolving 0.25 g of polymer powder in 12.25 g of DMF by stirring using a magnetic bar until the solution became homogeneous. 2.4 ml of the polymer dope solution was dropped on the polished side of an α-alumina support using a micropipette, fully covering the support surface. Immediately after, the sample was placed in a vacuum oven pre-heated at 150° C. and baked at the same temperature for 24 h under vacuum to evaporate DMF. The sample was naturally cooled down to room temperature in the vacuum oven. Similar to 6FDA-DAM films, thin MATRIMID films coated on α-alumina disks were prepared using a 2 wt % MATRIMID dope solution in THF. 2.5 ml of the polymer dope solution was dropped on an α-alumina support. The solvent (THF) was slowly evaporated in a sealed Teflon cup for 5 h, vitrifying MATRIMID films. The films were further dried at 150° C. for 24 h under vacuum to completely remove residual solvent.

Fabrication of Mixed-Matrix Membranes Via Polymer-Modification-Enabled In Situ Organic Framework Formation (PMMOF) Process To hydrolyze a polyimide-based polymer film coated on an α-alumina support, an aqueous sodium formate solution was prepared by dissolving 100 mmol of sodium formate in 30 ml of deionized (DI) water. A supported polyimide film prepared above was vertically placed using a custom-made Teflon holder in a Teflon-lined autoclave containing the sodium formate solution. The autoclave was then heated at 120° C. for 5 h. After cooling down the autoclave at room temperature for 2 h, the hydrolyzed polymer film (i.e., PAA(polyamic acid)-Na salt film) was removed and rinsed in 80 ml of DI water overnight in a lab shaker to completely remove physically absorbed Na ions and formate ions. Na ions in the hydrolyzed polymer were then exchanged with Zn ions (Cu ions for HKUST-1 or Co ions for ZIF-67) by vertically immersing the film into a metal ion solution. The metal ion solution was prepared by dissolving 16 mmol of zinc nitrate hexahydrate (copper(II) nitrate trihydrate for HKUST-1 or cobalt(II) nitrate hexahydrate for ZIF-67) in 40 ml of water at room temperature for an hour. After the ion-exchange step, the zinc containing sample (i.e., PAAZn salt film) was quickly rinsed in 80 ml of methanol for 10 sec and then positioned vertically in a Teflon-lined autoclave containing an organic ligand solution. Any organic linker suitable for MOF or ZIF structures may be used. In this instance the ligand solution was prepared by dissolving 28.4 mmol of 2-methylimidazole (9.47 mmol of 1,3,5-benzene tricarboxylic acid for HKUST-1) in 30 ml of methanol. The zinc containing film was then treated in the ligand solution at 40° C. for 2 h, followed by 2 h of cooling to room temperature. The resulting ZIF-8 containing film was washed in fresh methanol overnight. To minimize surface tension during solvent evaporation, the sample was subjected to solvent exchange in methanol and in hexane for 30 min each. The sample was then dried at room temperature for 1 h and then at 60° C. for over 2 h. Lastly, the sample was thermally imidized at 250° C. for 4 h in a convection oven.

Polymer Swelling Experiments

A polymer swelling experiment was conducted by soaking a free-standing polymer in water for 1 h and in methanol for 2 h at room temperature. Weight of the swollen polymer was measured after carefully blotting the surface using Kimwipes.

Characterizations

Scanning electron microscope (SEM) images were collected using a JEOL JSM-7500F at acceleration voltage of 5 keV and working distance of 15 mm after freeze fracturing samples in liquid nitrogen. Transmission electron microscope (TEM) was conducted by JEOL JEM-2010 TEM at an operation voltage of 200 keV. X-ray photoelectron spectroscopy (XPS) was performed by an Omicron ESCA+ with Mg X-ray source at 300 W. Crystallinities and phases of samples were determined by X-ray diffraction (XRD) patterns using a Miniflex II (Rigaku) with Cu-Kα radiation ($\lambda$=1.5406 Å) in the 2 θ range of 5-40°. Attenuated total reflectance Fourier transform infrared (ATR-FTIR) spectra were collected by Nicolet iS5 spectrophotometer equipped with iD7 ATR (Thermo Scientific) at a resolution of 2 $cm^{-1}$ with 16 scans in the span of 4000-400 $cm^{-1}$. Thermogravimetric analysis (TGA) using a Q50 (TA instruments) was conducted from 25° C. to 800° C. at the heating rate of 10° C. min$^{-1}$ under air flow of 60 cm$^3$ min$^{-1}$. Before conducting TGA, each sample was dried at 100° C. for 12 h under vacuum to remove any absorbed water.

Gas Permeation Measurements

Gas permeation properties of pristine polyimide membranes as well as mixed-matrix membranes were measured using the Wicke-Kallenbach technique at room temperature under atmospheric pressure using a binary equimolar propylene/propane gas mixture. A feed gas mixture was provided at 20 cm$^3$ min$^{-1}$ while the permeate side was swept using argon at 20 cm$^3$ min$^{-1}$. Steady-states were declared after 12 h of operation when difference in the measured propylene permeance of a sample was less than 1% in an hour interval. Composition of the permeated gases was determined by gas chromatography (GC 7890A, Agilent) equipped with a flame ionized detector (FID) and a HP-plot Q column.

Quantification of In Situ Grown ZIF-8 Nanoparticles in a Polymer

The amount of ZIF-8 in situ grown in a polymer was determined using TGA measurement by thermally oxidizing PI/ZIF-8 samples under air flow. The resulting residues are assumed to ZnO since organic components including polymer and linkers of ZIF-8 are almost completely decomposed at the final temperature of 800° C. (1-3). There are two possible sources generating ZnO upon the thermal oxidization: ZnO (I) from ZIF-8 and ZnO (II) resulting from the oxidization of remaining free and coordinated Zn ions. Also, ZnO (III) formed by the Zn ions detached from polymer coordination bonds during the imidization can already exist in a polymer. To clarify the quantity of ZnO (I), the amount of residue of PI/ZIF-8 was subtracted from that of washed PAA-Zn consist of ZnO (II). Moreover, it should be mentioned that the ZIF-8 on the polymer surface, which does not give influence upon gas transport, was removed by the surface acid treatment. The quantity of ZIF-8 inside polymer, hence, was calculated by dividing the amount of ZnO (I) by that of pure ZIF-8, as follows:

$$ZIF-8 \text{ fraction in polymer} = \frac{(ZnO \text{ from } PI/ZIF-8) - (ZnO \text{ from } PAA-Zn)}{ZnO \text{ from pure } ZIF-8} \quad \text{Eq. 1}$$

Example 2

PMMOF Process

Concept

The key concept of the polymer-modification-enabled in situ metal-organic framework formation process is to enlarge and modify polymer free volumes where MOF precursors can be accommodated, thereby providing ideal environments inside polymer for in situ growth of MOF nanoparticles. As illustrated in FIG. 1A, the first step of the process is hydrolysis of a polyimide by cleaving heterocyclic imide rings in a base solution (i.e., deimidization). Tsuruoka et al. (21) hydrolyzed a KAPTON in a KOH solution. In contrast, it was found to be more controllable to carry out hydrolysis in a weaker base such as sodium formate. This deimidization step turns a polyimide (PI) into a poly(amic acid) sodium salt (PAA-Na) (FIG. 1B). The subsequent step is exchange of Na ions with Zn ions, forming poly(amic acid) zinc salt (PAA-Zn) (FIG. 1C). Solvothermal treatment of the PAA-Zn in an organic linker, 2-methylimidazole, solution leads to in situ formation of ZIF-8 nanoparticles in the PAA-Zn (PAA-Zn/ZIF-8) (FIG. 1D). Finally, the PAA-Zn containing ZIF-8 nanoparticles is thermally re-imidized, resulting in a PI/ZIF-8 composite film (FIG. 1E).

FIGS. 1F-1I show a schematic illustration of PMMOF where a pristine KAPTON polyimide (KAP) hydrolyzed with potassium hydroxide, KOH. Only a part of the polyimide (typically less than 5 µm) was hydrolyzed. Upon the in situ solvothermal treatment of the Zn$^{2+}$-polyamate salt in a Hmim linker solution, only free Zn$^{2+}$ ions elute from the free volume, resulting in the formation of continuous ZIF-8 layers on polymer surface as well as ZIF-8 crystals inside the polymer.

Hydrolysis

The first hydrolysis step, where a polyimide (PI) is transformed to a poly(amic acid)(PAA), is essential to the success of the PMMOF process. To show the importance of the hydrolysis, two different PIs, MATRIMID and 6FDA-DAM, were tested with and without hydrolysis. Without hydrolysis, no ZIF-8 crystals were formed in the MATRIMID while there were very little ZIF-8 crystals appeared in the 6FDA-DAM (FIG. 2A). In a stark contrast, however, substantial amounts of ZIF-8 crystals were found in both of the hydrolyzed PIs, indicating the critical role of the hydrolysis (i.e., imide ring opening). It is surmised that when imide rings are open by the hydrolysis, polymer backbone chains become more flexible, thereby enlarging the free volumes as well as making the polymer more hydrophilic. Consequently, Zn ions can easily diffuse inside, eventually leading to formation of ZIF-8 crystals inside the polymers. As can be seen in FIG. 2A, it is clear that under the same hydrolysis condition, 6FDA-DAM is more amenable to the PMMOF than MATRIMID likely due to the fact that it has inherently larger free volume (i.e., less densely packed). Furthermore, 6FDA-DAM is known for its excellent gas separation performance and in particular for its $C_3H_6/C_3H_8$ separation property match with ZIF-8 in mixed-matrix membranes. Based on these, 6FDA-DAM was chosen as a model polyimide.

Figure 2B:
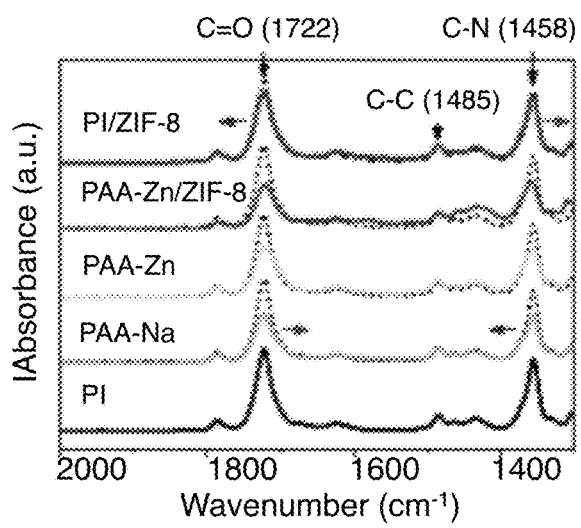

The degree of deimidization of 6FDA-DAM can be controlled by simply changing the hydrolysis time in sodium formate at a fixed temperature of 120° C. Upon hydrolysis, as presented in FIG. 2B, it was observed slight shifts in the ATR-IR peaks at 1356-1361 cm$^{-1}$ and 1720-1724 cm$^{-1}$ assigned to the C—N stretching and the symmetric C=O stretching in the imide rings, respectively. Also, the relative intensities of those peaks decreased comparing with that of the C—C stretching in the aromatic rings at a wavenumber of 1485 cm$^{-1}$ (FIG. 2B). To quantify imidization, the degree of imidization (DI) was commonly used as an indicator and calculated as below (16-18):

$$\text{Degree of imidizaition (\%)} = \frac{(A_{1358}/A_{1485})_{specimen}}{(A_{1358}/A_{1485})_{standard}} \times 100 \quad \text{Eq. 2}$$

where A is the IR absorbance and the subscripts are the wavenumbers of the IR peaks. A pristine 6FDA-DAM film was used as a standard, assuming 100% imidization. Conversely, the degree of deimidiziation (DD) was calculated by using the following equation:

$$\text{Degree of deimidizaition}(\%) = \left[1 - \frac{(A_{1358}/A_{1485})_{specimen}}{(A_{1358}/A_{1485})_{standard}}\right] \times 100 \quad \text{Eq. 3}$$

Figure 2C:
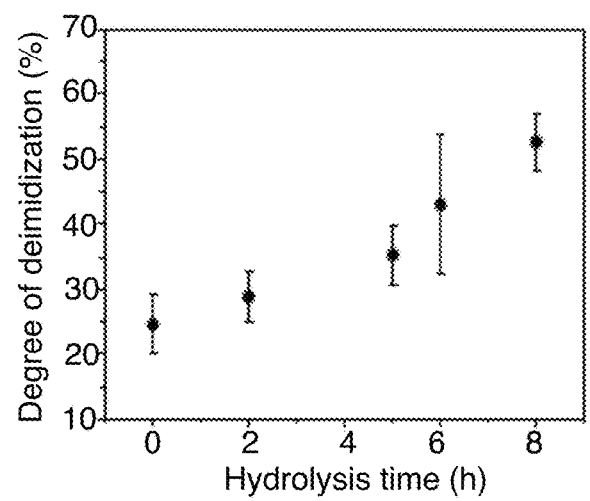
Figure 2D:
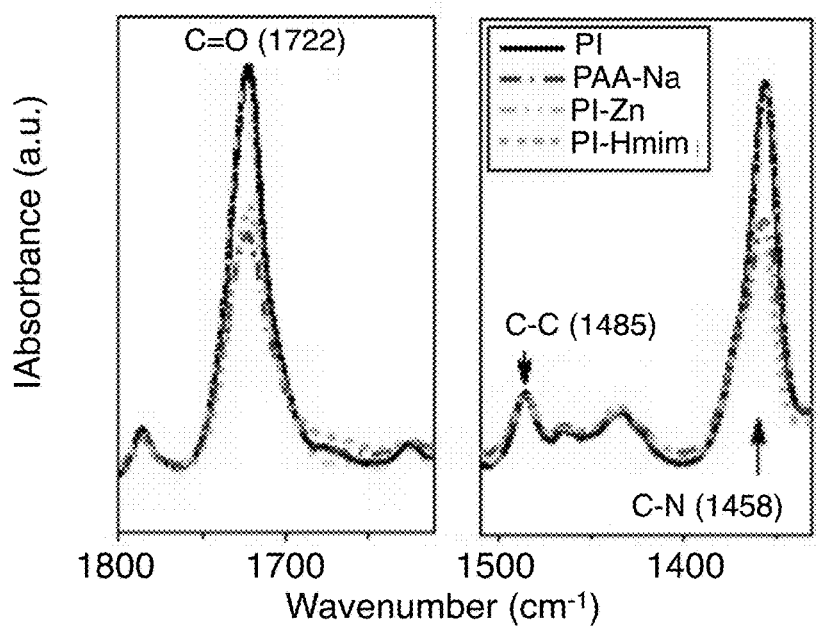
Figure 2E:
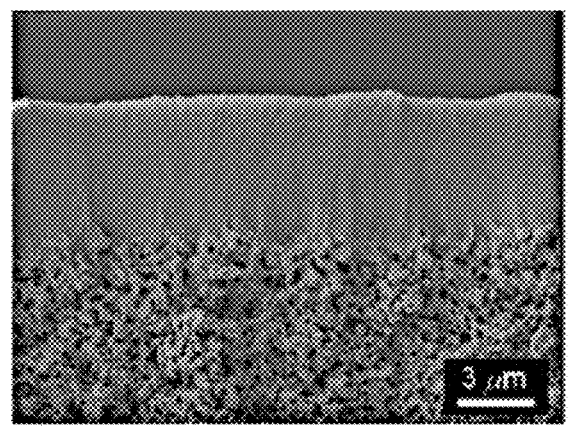
Figure 2F:
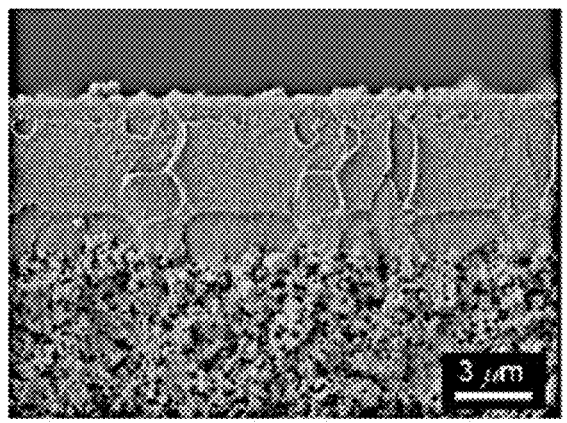
Figure 2G:
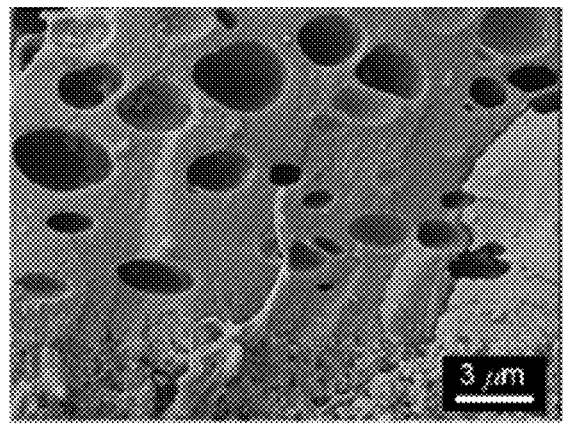

The DD was augmented with an increase in the hydrolysis time as shown in FIG. 2C. It turned out that 6FDA-DAM was hydrolyzed not only by sodium formate but also by Hmim. Weakly basic Hmim hydrolyzed the polymer as much as a DD of 24.6±4.6% while the zinc solution did not affect hydrolysis (FIG. 2D). As the DD increased, PAA-Na formation was promoted, consequently increasing the uptake of Zn ions, thereby enhancing formation of PAA-Zn. However, too high DD can damage and eventually disintegrated polymer films. It was found that when the DD was greater than ~50%, there formed undesirable micro-voids which are detrimental to gas separations (FIGS. 2E-2G). For these reasons, an optimized hydrolysis time was set to 5 h with a degree of deimidization of 35.3±4.6%.

Zinc Ion Exchange

Figure 3A:
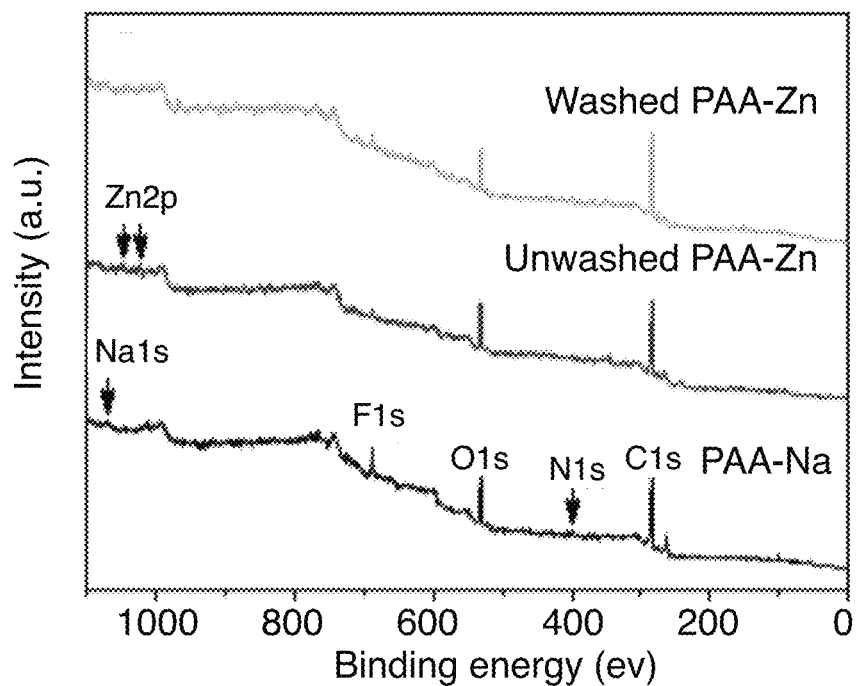
FIGS. 3A-3D are XPS spectra of PAA-Na and PAA-Zn samples before and after extensive washing after zinc ion exchange.
Figure 3B:
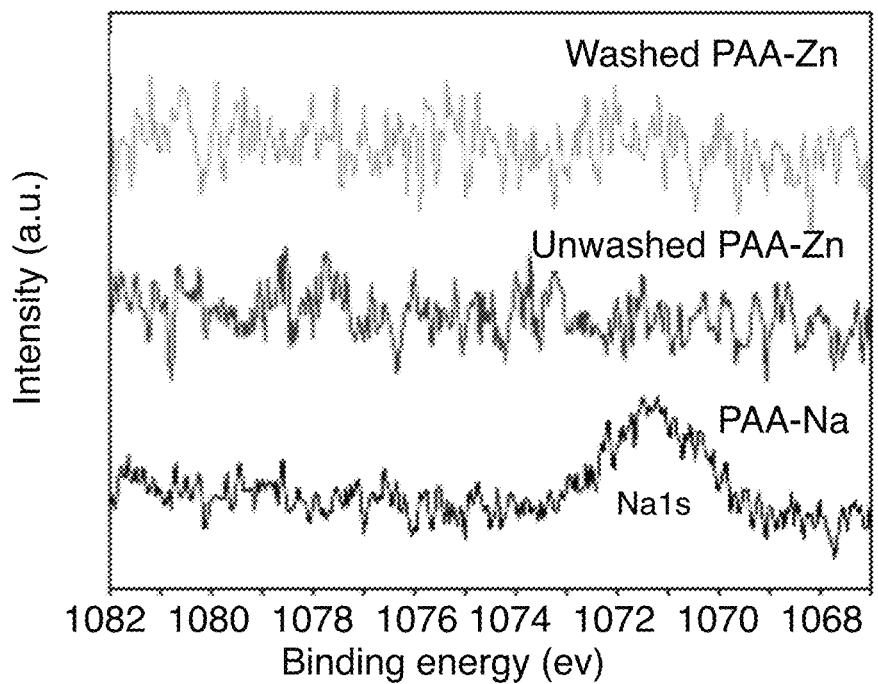

Upon ion exchange, ionically coordinated monovalent Na ions in PAA-Na are replaced with divalent Zn ions, metal centers of ZIF-8, consequently forming PAA-Zn. To confirm complete exchange of the Na ion coordinated to the polymer, an elemental analysis using XPS was performed. As shown in FIGS. 3A-3B, the Na s1 peak in the span of 1069-1075 eV, appeared in the PAA-Na, was not detected in the PAA-Zn. The amounts of Na in the PAA-Na and Zn in the PAAZn were estimated ~0.62 at % and ~1.27 at %, respectively as shown in Table 1.

TABLE 1

Atomic percentages of elements for PAA-Na & PAA-Zn samples measured by XPS

| Unit: At % | Carbon | Oxygen | Nitrogen | Fluorine | Sodium | Zinc |
|---|---|---|---|---|---|---|
| PAA-Na | 71.20 | 18.36 | 3.08 | 5.84 | 0.62 | 0.00 |
| Unwashed PAA-Zn | 71.97 | 19.84 | 3.83 | 3.10 | 0.00 | 1.27 |
| Washed PAA-Zn | 75.54 | 17.17 | 2.99 | 3.13 | 0.00 | 0.29 |

Figure 3C:
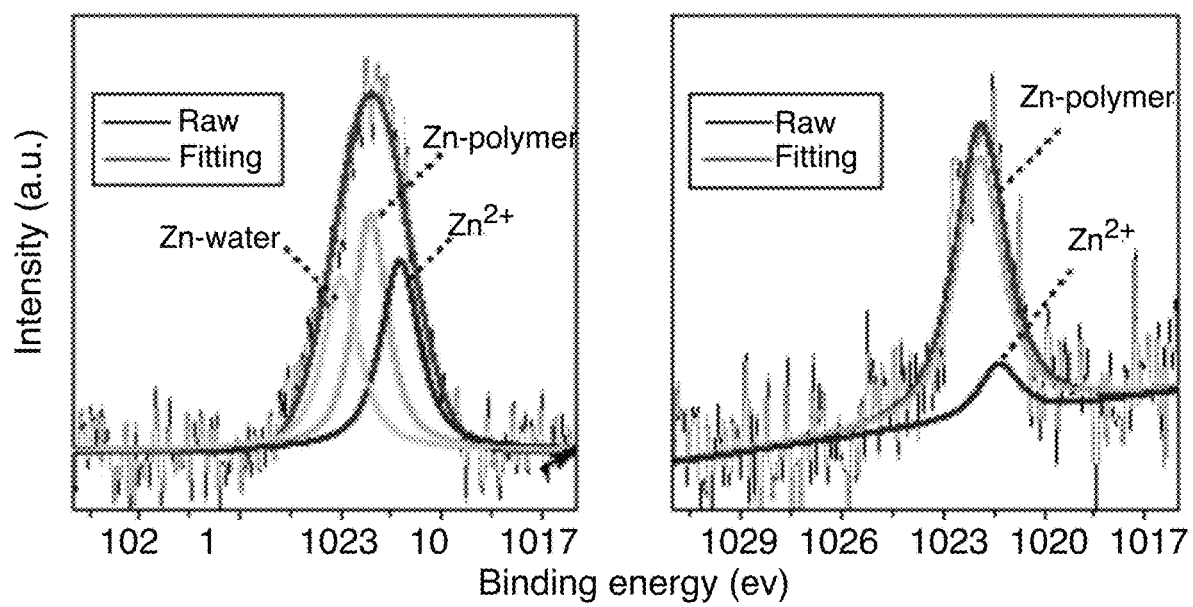

The ratio of Na to Zn was ~0.5:1, which is much lower than the expected stoichiometric ratio of Na to Zn of 2:1, indicating the presence of excess Zn ions in the PAA-Zn. To verify the presence of excess Zn ions, the narrow scan of the XPS spectra of Zn 2p3/2 in an as-prepared PAA-Zn was compared to that of the PAAZn extensively washed in methanol. Excess Zn ions that are not coordinated are expected to be removed by extensive washing. The Zn 2p3/2 peak of the as-prepared PAA-Zn was deconvoluted into three peaks at 1023.0 eV, 1022.1 eV, and 1021.3 eV, which were assigned to Zn ion coordinated to water (Zn-water), Zn ion coordinated to polymer (Zn-polymer), and free Zn ion ($Zn^{2+}$), respectively (FIG. 3C, left). In contrast, the deconvoluted Zn 2p3/2 peaks of the extensively washed sample showed only two peaks, Zn-polymer and $Zn^{2+}$, indicating that Zn-water ions were completely washed out by methanol (FIG. 3C, right). In addition, the intensity of the $Zn^{2+}$ comparing with that of the Zn-polymer substantially decreased upon washing, confirming that the excessive Zn ions were present in the forms of free ions as well as ions coordinated with water. The atomic percentage of Zn in the PAA-Zn after washing displayed a noticeably lower value of 0.29 at % compared to that of the unwashed PAA-Zn (1.27 at %). For the PAA-Zn sample with excessive Zn ions removed, the Na-to-Zn ratio was close to the stoichiometric ratio of 2:1, confirming that coordinated Na ions were replaced by Zn ions upon the ion-exchange.

Figure 3D:
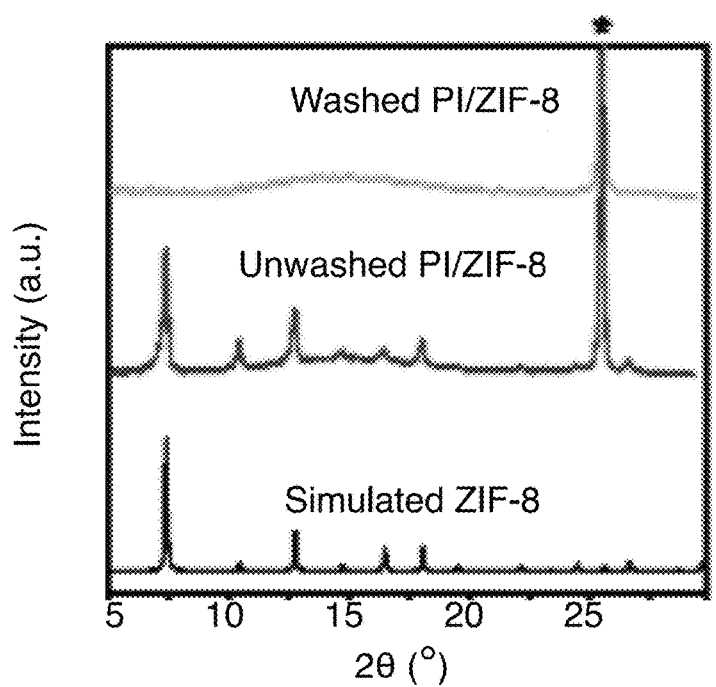

It was determined which one(s) of the three zinc sources (i.e., Zn-water, Zn-polymer, and free $Zn^{2+}$) was responsible for the in situ formation of ZIF-8 inside polymer. If polymercoordinated Zn ions (i.e., Zn-polymer) are a primary zinc source for ZIF-8 formation, even after extensive washing right after ion exchange, the sample is expected to contain ZIF-8 crystals once the PMMOF process is completed. As seen in FIG. 3D, however, the washed PI/ZIF-8 sample (i.e., washed after ion exchange) showed no diffraction peaks while the unwashed PI/ZIF-8 presented ZIF-8 peaks. An XPS analysis clearly showed the presence of mostly Zn-polymer in the sample washed after ion exchange (FIG. 3C). This result strongly suggests that Zn ions that were not coordinated with polymer were responsible for ZIF-8 formation. This is ascribed to the fact that Zn-polymer is not as mobile due to their strong electrostatic interactions with the carboxylate anions in polymer via multiple bonds (i.e., one Zn ion interacts with two carboxylate anions). These multiple coordinations might create crosslinking-like states in polymer (19-21). This is quite contrary to the observations made by Tsuruoka et al. (9) that coordinated Al ions were responsible for MIL-53 formation on hydrolyzed KAPTON surfaces. This difference can be explained by the fact that their solvothermal ligand treatment was much more aggressive (under microwave heating at 200° C. for 1 h) than ours (under convective heating at 40° C. for 2 h), which might have provided enough energy to release strongly coordinated Al ions.

2-methylimidazole (Hmim) Treatment

Figure 4A:
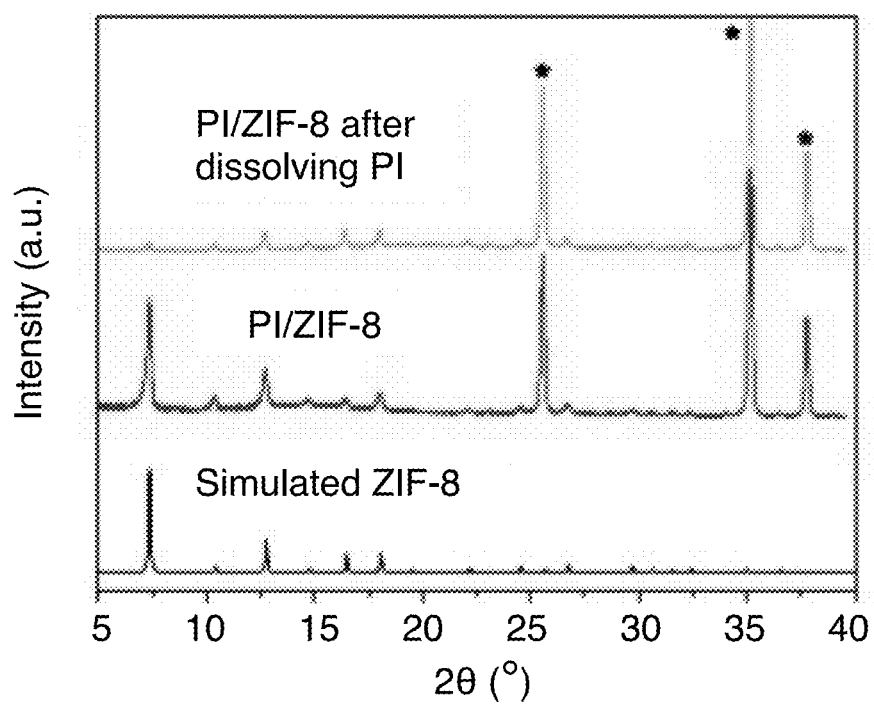
FIGS. 4A-4F are XRD patterns and SEM images of PUZIF-8.
Figure 4B:
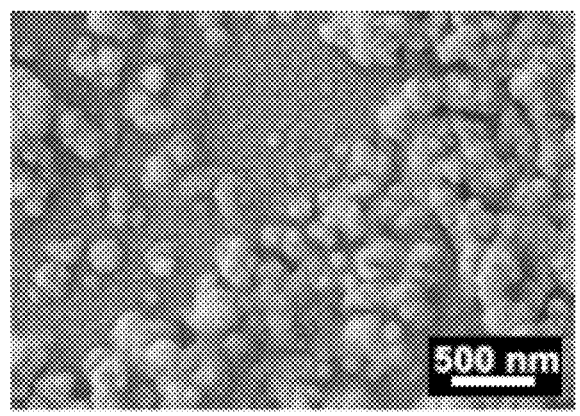
Figure 4C:
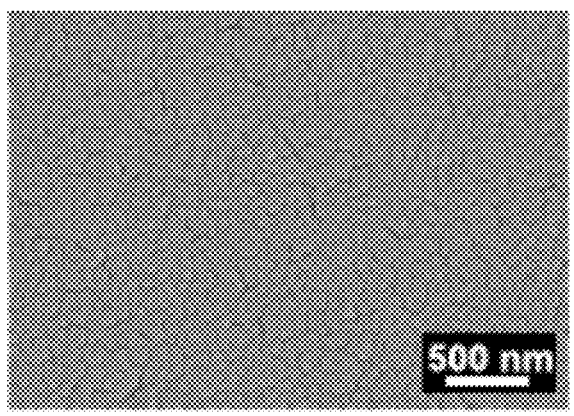
Figure 4D:
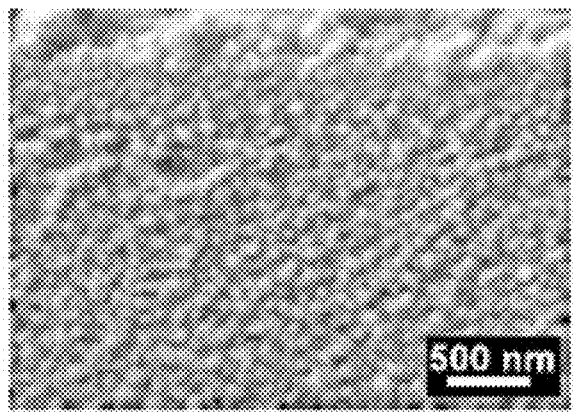
Figure 4E:
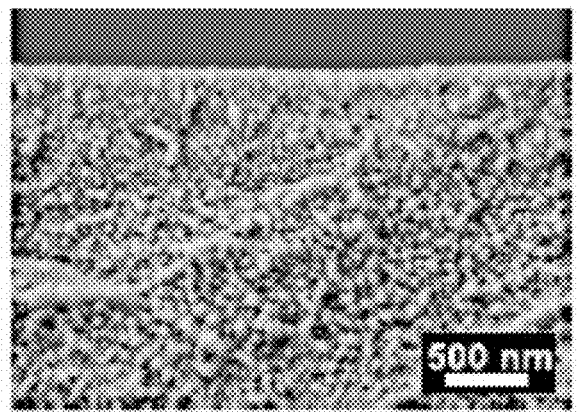
Figure 4F:
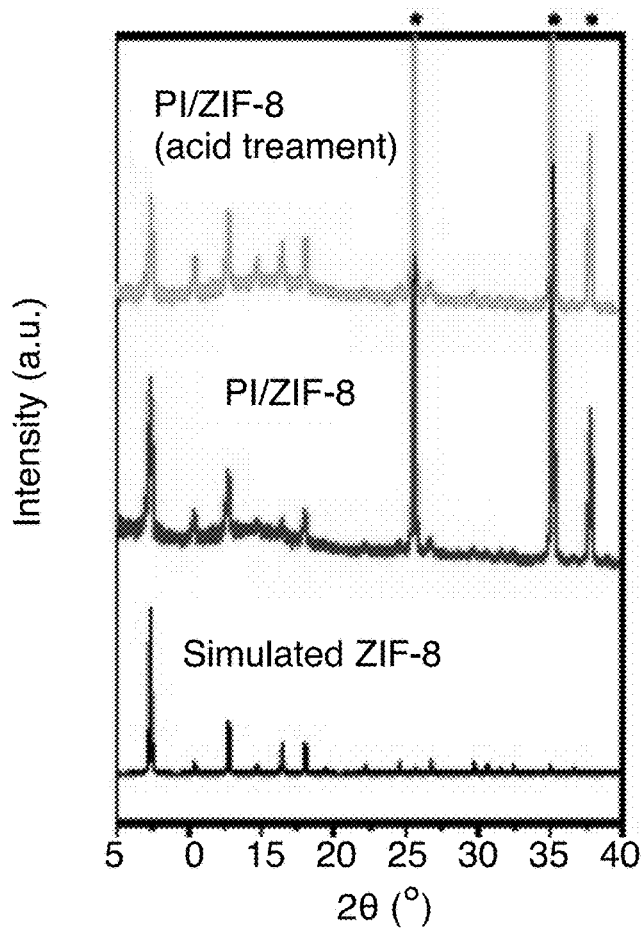

Though formation of ZIF-8 crystals upon the Hmim treatment was confirmed by XRD diffraction patterns (FIGS. 2A, 3D), it is interesting to determine the locations of the crystals, i.e., inside polymer, on polymer surface and/or in the porous α-alumina support. First, the absence of ZIF-8 in the α-alumina support was verified by 1) dissolving the polymer from the PI/ZIF-8 in 80° C. NMP for one day and 2) confirming a negligible amount of ZIF-8 in the support (FIG. 4A). Second, the top surface of the PI/ZIF-8 showed the growth of ZIF-8 on the polymer surface (FIGS. 4B-4C). While no inter-grown ZIF-8 layer was formed unlike the case of Tsuruoka et al., (21) it was observed that ZIF-8 clusters were sparsely distributed and merged with polymer matrix (FIGS. 4B-4F). To examine formation of ZIF-8 within the polymer, the surface-bound crystals were removed by gently wiping the surface with a diluted acid solution (i.e., 0.1 M HNO3). As exhibited in FIGS. 4D-4E, even though the ZIF-8 crystals on the surface were entirely eliminated by the surface acid treatment, the characteristic peaks of ZIF-8 were maintained (FIG. 4F). This confirms that most of ZIF-8 nanoparticles were grown inside the polymer during the PMMOF process, thereby forming mixed-matrix membranes.

Imidization

Figure 5A:
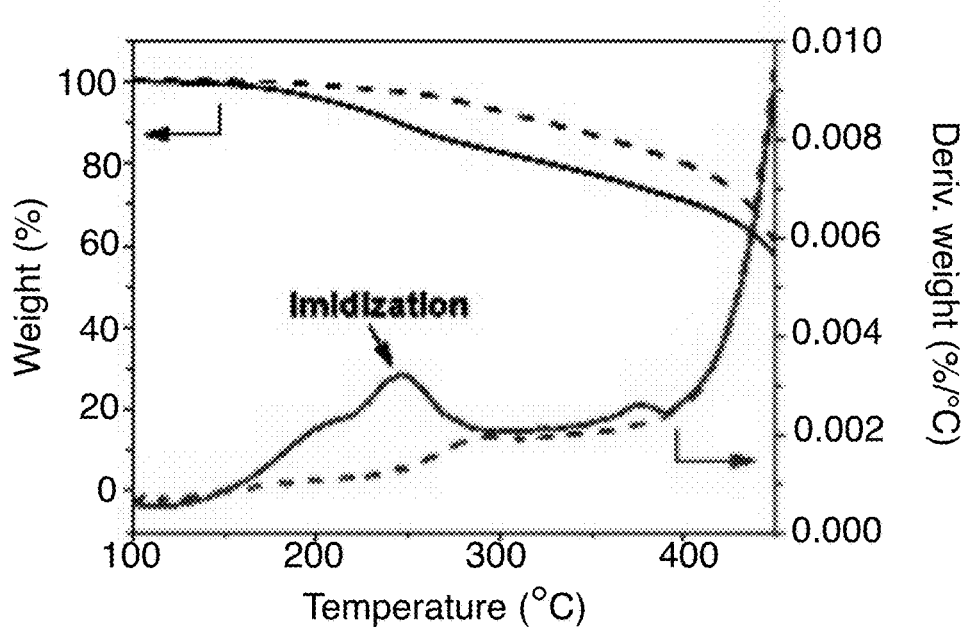
FIGS. 5A-5C show TGA curves and corresponding derivative curves before imidization of PAA-Zn/ZIF-8 (FIG. 5A, solid) and after imidization of PI/ZIF-8 (FIG. 5A, dashed) and the time-dependent evolution of the corresponding (110) XRD peaks before (FIG. 5B) and after (FIG. 5C) imidization.

For membranes to perform stably, the deimidized polymer needs to be re-imidized. Nevertheless, the very stable coordination bond between zinc cations and carboxylate anions is expected to hamper complete imidization. Previous studies (18) showed that Zn ions coordinated polymer (PAA-Zn), in particular, exhibited a lower degree of imidization (DI) (Eq. 2) than PAA as well as PAAs coordinated with other metal ions. Kim et al. (18) found that a relatively high imidization temperature (≥250° C.) was required in order to disengage coordinated Zn ions from chelate complexes and to form imide groups. As shown in the TGA weight loss and its derivative curve in FIG. 5A, the imidization started from ~150° C. with the maximum rate at ~250° C. The degree of imidization was attained at 88.0±5.0% by conducting the thermal imidization at 250° C. for 4 h (FIG. 2B). While detached Zn ions during the re-imidization were possibly transformed into ZnO, it was not observed in this study likely due to the very small amount.

Figure 5B:
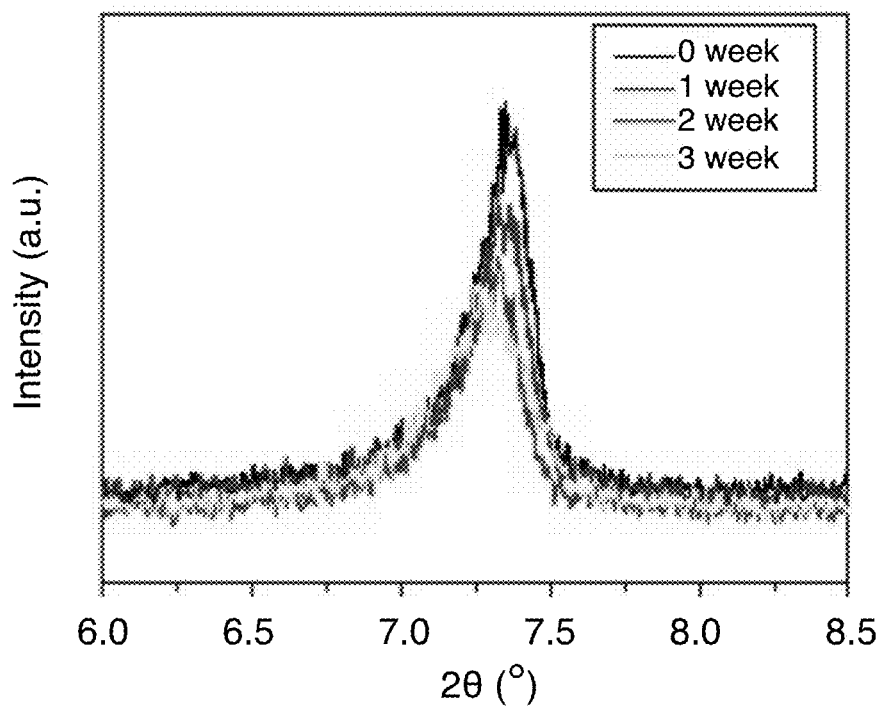
Figure 5C:
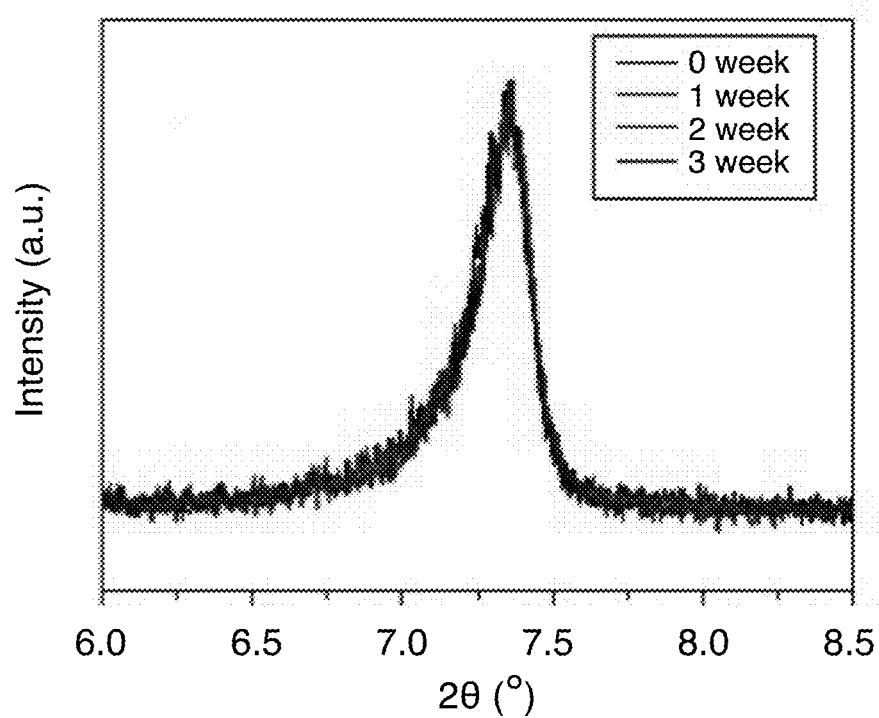

The (110) peak intensity of the PAA-Zn/ZIF-8 gradually decreased over several weeks as shown in FIGS. 5B-5C. The acidic components of PAA presumably degraded ZIF-8 nanoparticles since ZIF-8 is known unstable in an acid condition (22). The acidic components of PAA were generated probably by some carboxylic acid groups formed during the PMMOF process. This observation is consistent with the previous study of a ZIF-8 containing MMM with a benzoic acid containing polymer (i.e., 6FDA-DAM/DABA) (23). Upon imidization, however, the (110) peak intensity of the PI/ZIF-8 remained unchanged during the same time span (FIG. 5C), strongly indicating importance of post-imidization in stabilizing the membranes.

Example 3

Spectroscopy and X-Ray Diffraction of Pristine KAPTON Film and ZIF-8 Films

Figure 6A:
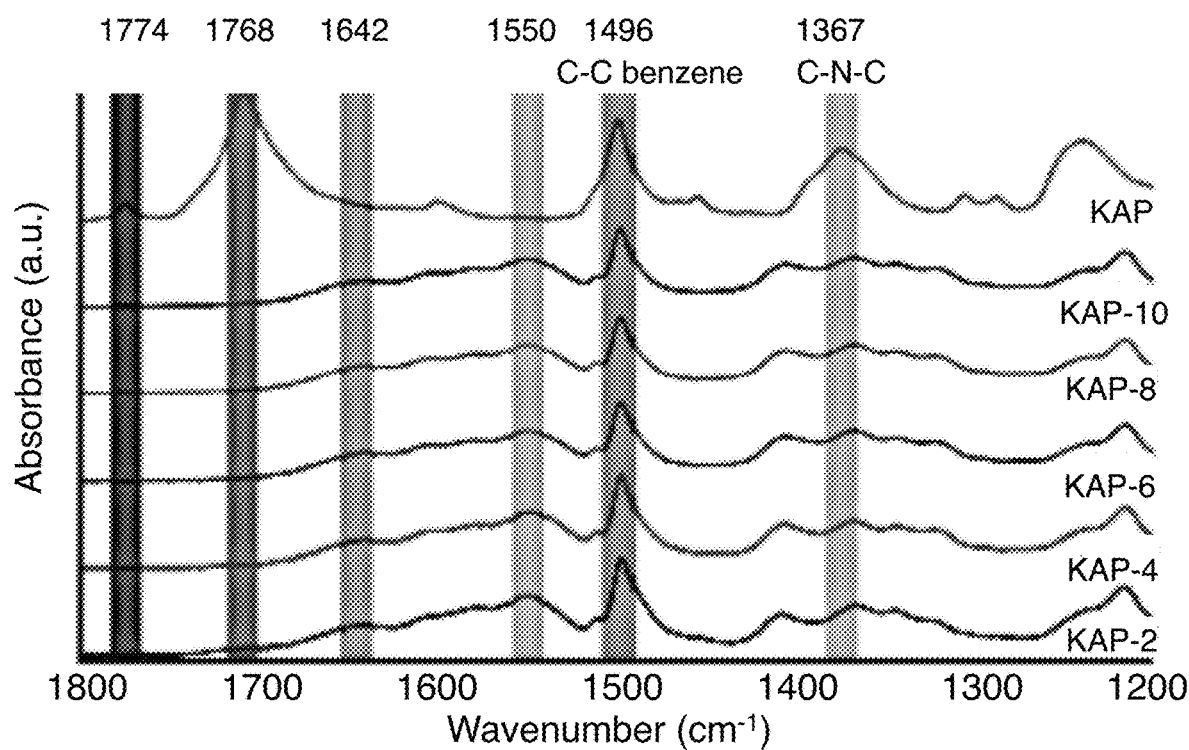
FIGS. 6A-6D show ATR-FTIR spectra, relative intensity and PXRD patterns of KAPTON films.

FIG. 6A presents the attenuated total reflection Fourier transform infrared (ATR-FTIR) spectra of pristine KAPTON and KOH treated (hereafter, KAP-X, where X represent KOH treatment time in minutes) films. The pristine film (FIG. 6A, S2) exhibited characteristic absorption bands at frequencies of 1774 $cm^{-1}$, 1708 $cm^{-1}$, 1496 $cm^{-1}$, and 1367 $cm^{-1}$ which correspond to symmetric C=O stretching, asymmetric C=O stretching, C=C benzene ring stretching, and C—N—C stretching, respectively[29]. Nucleophilic hydrolysis reaction by aqueous KOH led to imide-ring cleavage, thus resulting in reduction of C=O imide absorption bands (1774 $cm^{-1}$ and 1708 $cm^{-1}$). There appeared new broad peaks at 1500 $cm^{-1}$-1700 $cm^{-1}$, which were superposition of carboxyl groups complexed with K+(1500 $cm^{-1}$-1600 $cm^{-1}$), C=O amide (1642 $cm^{-1}$), and N—H amide (1550 $cm^{-1}$) modes of the resulting polyamic metal salt. A prolonged alkali hydroxylation reaction (>15 min), however, led to degradation of the substrates, thereby compromising their physical properties (24).

Figure 6B:
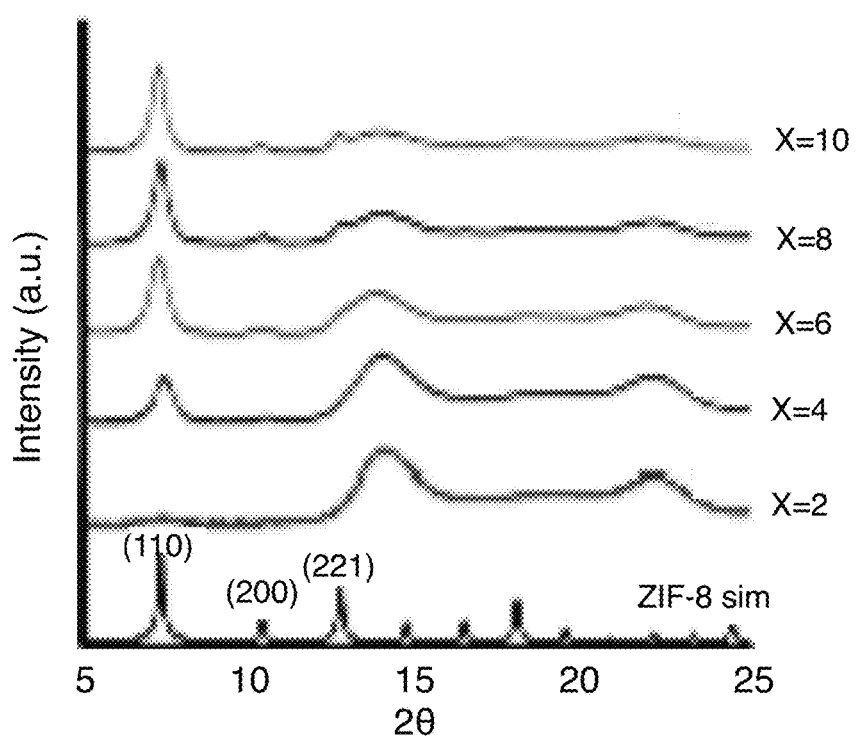

The $Zn^{2+}$-exchanged film (hereafter, KAP-x-Zn for x min in KOH) was solvothermally treated in a Hmlm linker solution to form continuous ZIF-8 layers (KAP-x-Zn-ZIF-8). Formation of phase-pure and crystalline ZIF-8 crystal layers on polymer substrates was confirmed by powder X-ray diffraction (PXRD) patterns (FIG. 6B). All samples exhibit superimposed diffraction patterns of ZIF-8 and pristine KAPTON film. Interestingly, the intensities of the characteristic ZIF-8 peaks increase with hydrolysis time. The samples exhibited relatively similar degree of peak broadening, indicating the formation of ZIF-8 nanoparticles regardless of hydrolysis time.

Figure 6C:
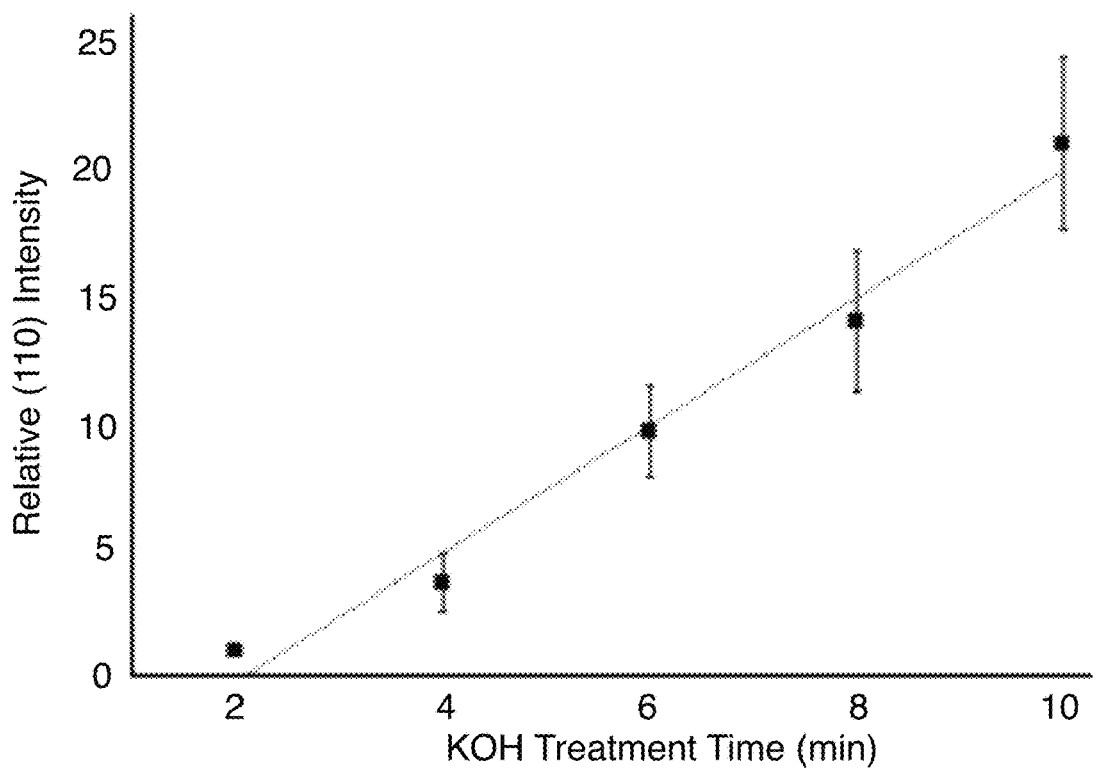

A plot of the relative (110) intensity provides a preliminary means to estimate the number of ZIF-8 nanocrystals formed as hydrolysis time increases. Since the concentration of $Zn^{2+}$ in the polymer is relatively low as compared to that of the linker, the number of ZIF-8 nanocrystals formed is expected to be limited by $Zn^{2+}$ concentration. The relative intensities of (110) reflection are, therefore, directly related to the relative increment in $Zn^{2+}$ content in the KOH-modified layer with respect to KOH treatment time. As shown in FIG. 6C, the relative (110) intensity increases linearly with degree of KOH hydrolysis, suggesting a systematic increment in the $Zn^{2+}$ content in the polymer substrates. This result agrees well with previous reports (21 25-26).

Figure 6D:
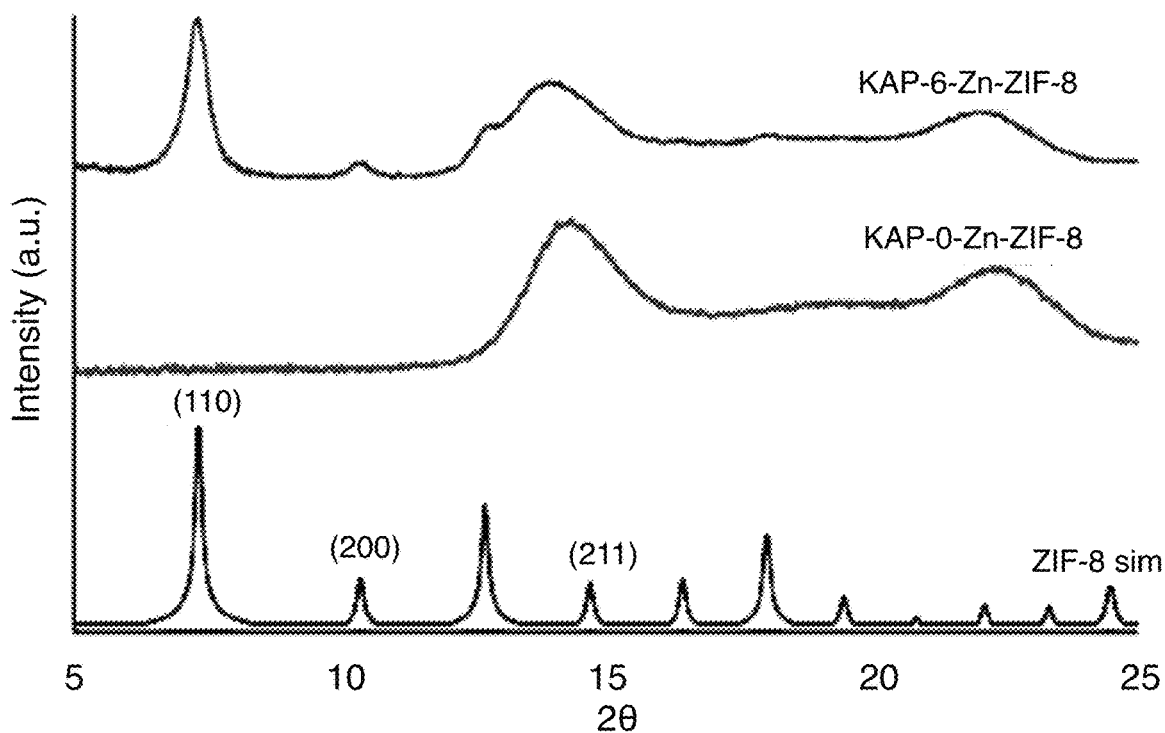

Extending the hydrolysis reaction increases the number of K+ in the modified layer. During ion-exchange process, the monovalent K+ cations were replaced with divalent $Zn^{2+}$ cations. Also, the presence of more carboxylates due to the longer KOH treatment enhances the hydrophilicity of the substrates, which facilitates the mobility and the amount of free Zn2+ ions into the polymer free volume. Films not subjected to the KOH treatment did not result in ZIF-8 crystals (FIG. 6D). This highlights the importance of imide-ring opening through the hydrolysis reaction and subsequent ion-exchange with Zn2+ for the nucleation and growth of ZIF-8 crystals.

XPS Spectroscopy and SEM Microscopy of $Zn^{2+}$-Doped Films

Figure 7A:
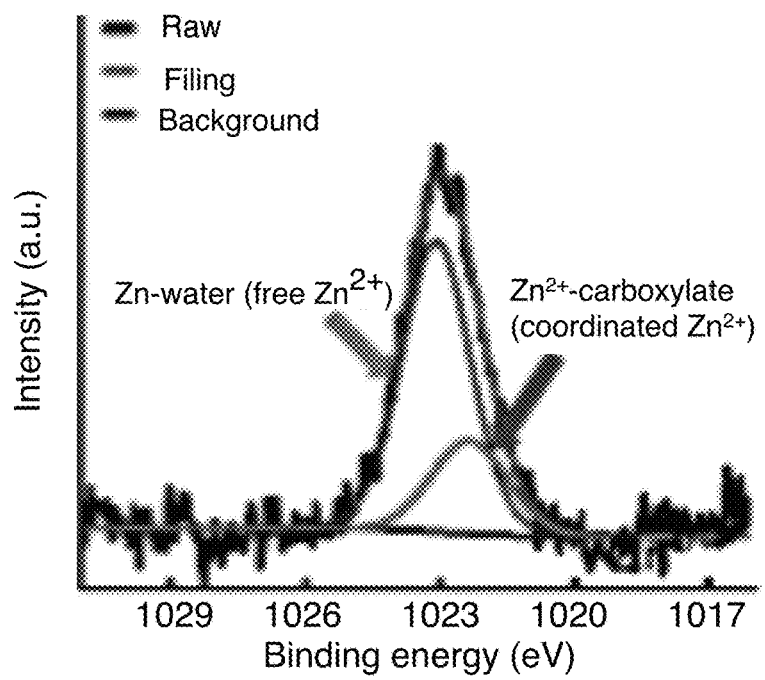
FIGS. 7A-7H are high resolution XPS spectra of the Zn2+-exchanged KAPTON film (FIG. 7A), top and cross-sectional SEM images of the films synthesized using polymer substrates immersed in KOH for 2 min (FIG. 7B), 4 min (FIG. 7C), 6 min (FIG. 7D), 8 min (FIG. 7E), and 10 min (FIG. 7F) and optical images (FIG. 7G) of ZIF-8 thin films with substrates subjected to different degrees of hydrolysis at 0, 2, 4, 6, 8, and 10 min.
Figure 7B:
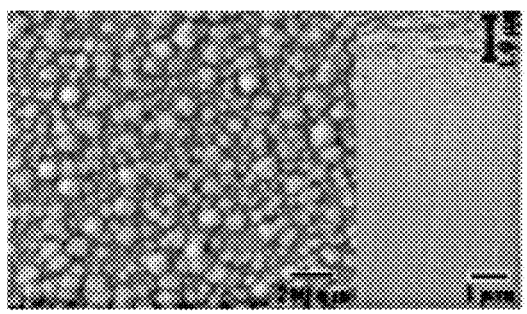
Figure 7C:
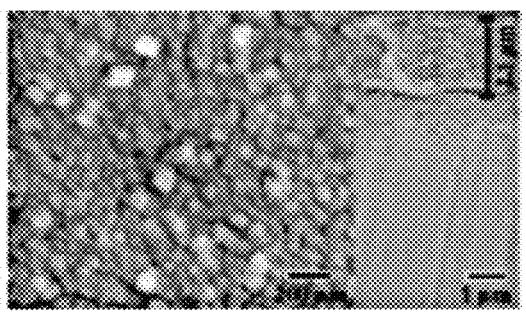
Figure 7D:
Figure 7E:
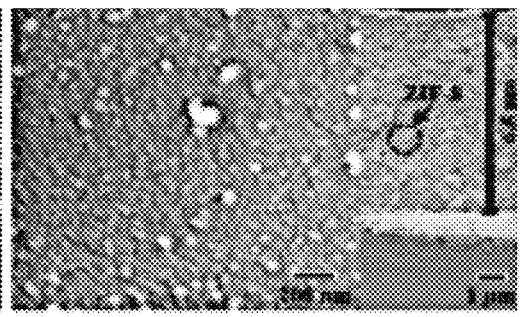
Figure 7F:

To identify Zn2+ bonding environment present in the polymer modified layer, X-ray photoelectron spectroscopy (XPS) was performed on the $Zn^{2+}$-doped films. FIG. 7A shows the XPS spectra of the Zn 2p3/2 core level of the $Zn^{2+}$-doped films. The deconvolution of the Zn 2p3/2 core level gives out two separate peaks at 1022.5 eV and 1023.1 eV that can be assigned to Zn-polymer (i.e., coordinated ions) and Zn-water (i.e., free ions) interaction, respectively (27-28). Control experiments were performed to gain insight into which of these $Zn^{2+}$ ions coordinating with carboxylic groups do not participate in the formation of ZIF-8 crystals. This is attributed to the fact that the coordinated $Zn^{2+}$ ions cannot be easily liberated possibly due to the relatively low concentration of counter cations (i.e., H+) present in the linker solution (pH ~9.9) and the use of relatively mild reaction temperature (120° C.). It is noted that Tsuruoka et al. (21) used microwave heating where the strong interaction between microwaves and coordinated cations in the polymer led to a rapid increase in the local temperature, thereby liberating coordinated $Al^{3+}$ ions.

Figure 7G:
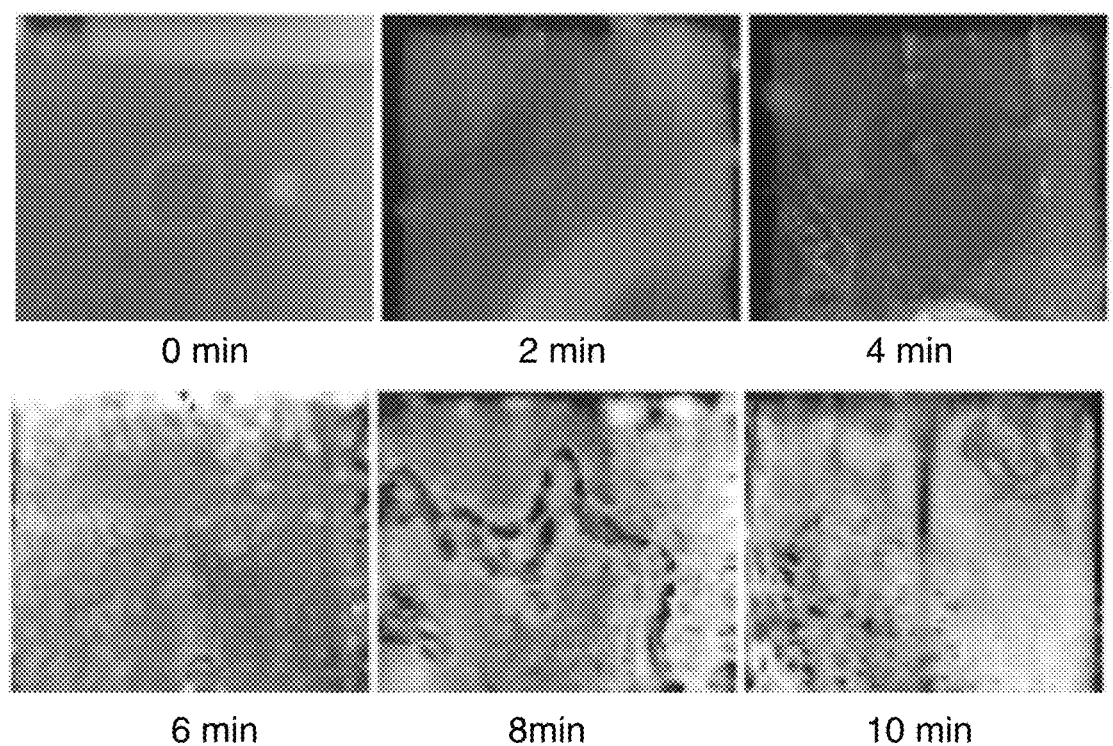
Figure 7H:
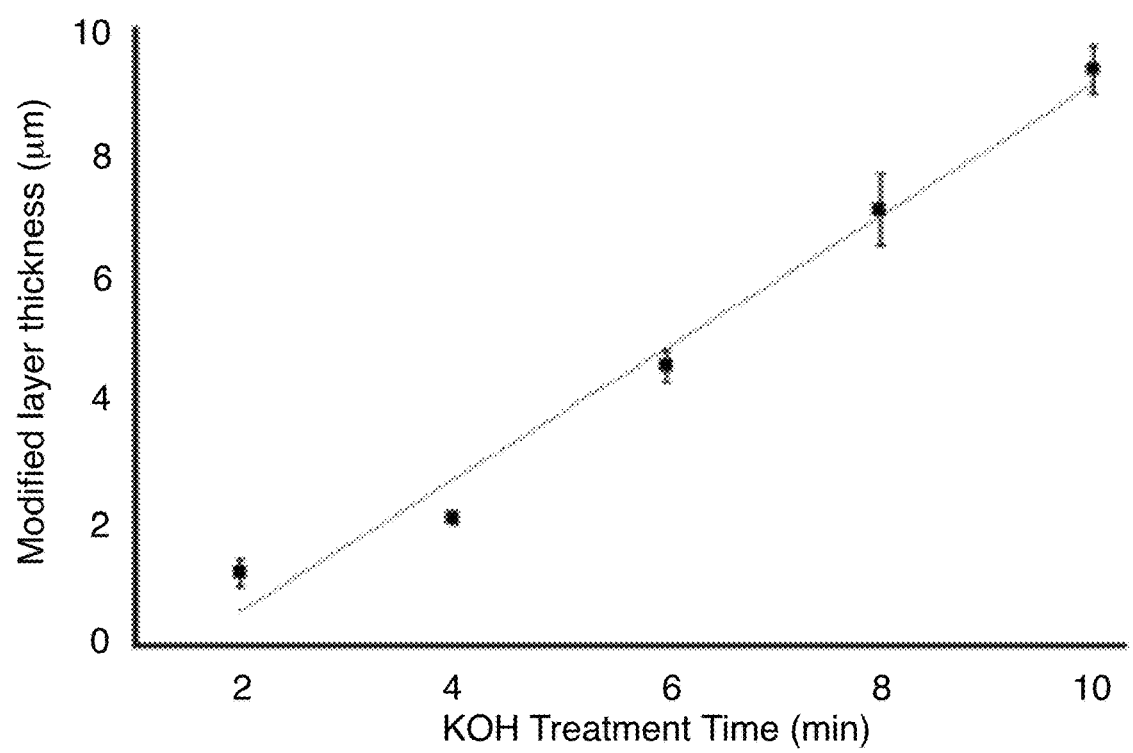

Scanning electron microscopy (SEM) images in FIGS. 7B-7F and optical images in FIG. 7G display the temporal evolution of KAP-X-ZN-ZIF-8 under different KOH treatment time. With the exception of KAP-2-ZN-ZIF-8, the samples formed continuous ZIF-8 crystal layers on top, implying that there is a minimum amount of metal-ion dopants required to form continuous ZIF-8 films on the substrate surface. The crystallite sizes were determined to be approximately 40.3±7.6 nm, which is comparable with the crystallite sizes calculated using the Scherer equation (33.7±7.0 nm). Cross-sectional SEM images revealed a very interesting morphology which has never been observed previously. As shown in the insets in FIGS. 7B-7F, larger ZIF-8 crystals were embedded (shown in circles) and uniformly distributed in the polymer matrix. This composite layer thickness increased linearly with KOH treatment time (FIG. 7H). It is contemplated that that formation of ZIF-8 crystals not only occur at the polymer-solution interface, but also occur inside the polymer possibly due to the slow elution rate of $Zn^{2+}$, thereby allowing Hmlm molecules to diffuse deep into and nucleate inside the KOH-modified layer. This feature may be useful for the in situ formation of composite films or mixed-matrix membranes with controlled thickness.

Figure 8A:
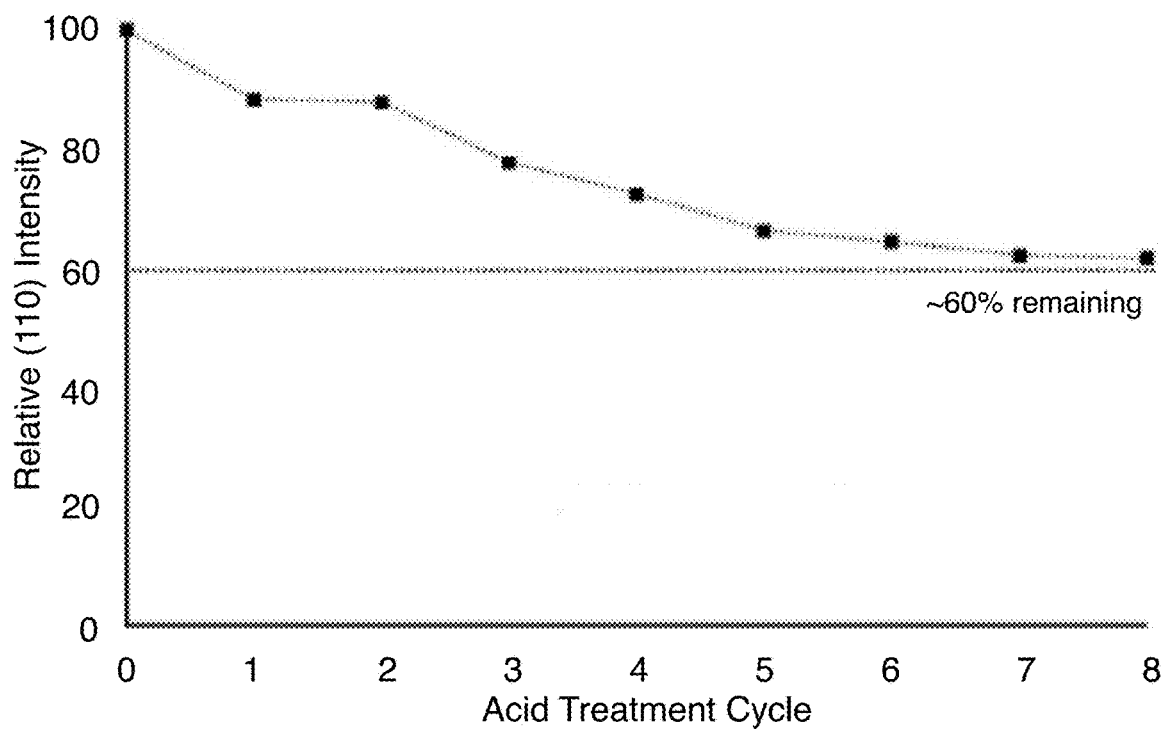
FIGS. 8A-8B show the relative (110) intensity of KAP-6-Zn-ZIF-8 (FIG. 8A) and KAP-2-Zn-ZIF-8 (FIG. 8B) samples as a function of acid treatment cycle.
Figure 8B:
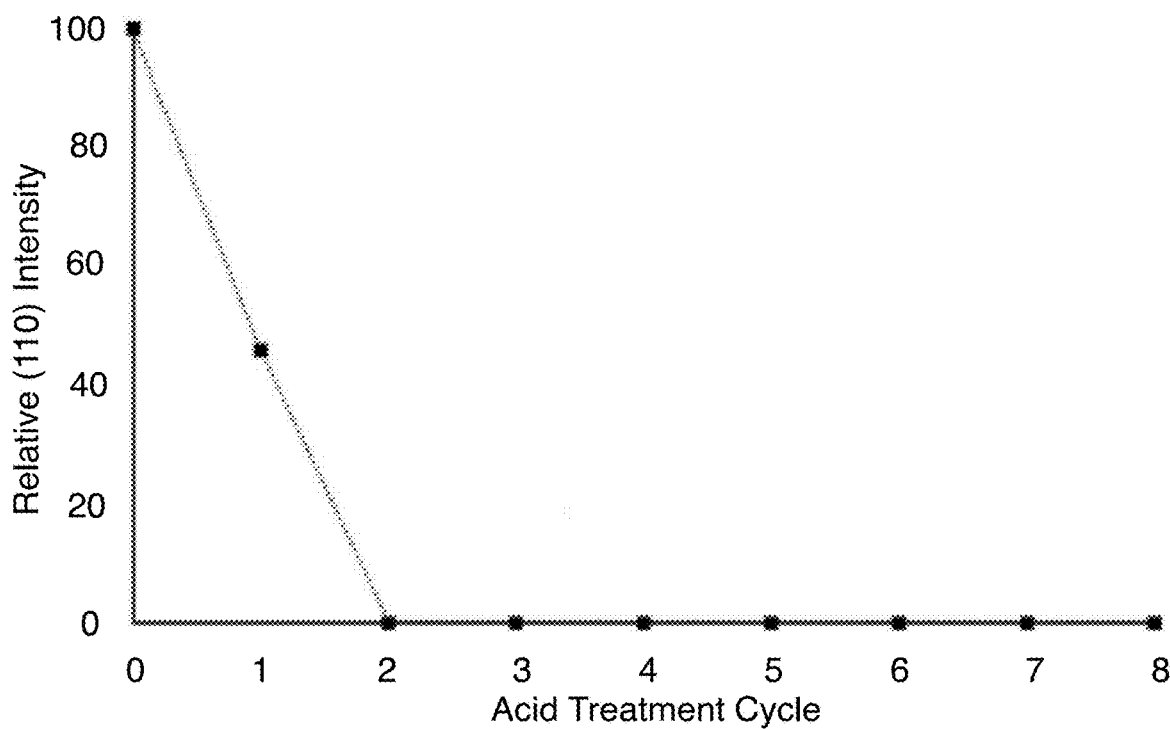

To confirm the formation of ZIF-8 crystals inside the polymers, a quick acid treatment was performed to remove surface-bound crystals from the samples. KAP-6-Zn-ZIF-8 samples were subjected to a diluted acid wipe (0.05 M $HNO_3$) for several cycles and PXRD patterns were collected after each cycle. A plot of the relative (110) intensity with the number of acid treatment cycles was constructed, serving as an indirect indicator of the relative amount of ZIF-8 formed inside vs. outside the polymer (FIGS. 8A-8B). After five acid treatment cycles, the relative (110) intensity remains almost constant (~60%). After initial removal of the surface-bound crystals, further removal of ZIF-8 by dilute $HNO_3$ is thwarted as the remaining ZIF-8 crystals are embedded and protected in the polymer matrix. Top SEM images (FIGS. 9A-9D) and energy dispersive X-ray (EDX) line scan analysis (FIGS. 9E-9F) performed on the surface of the acid treated samples confirmed a complete removal of the surface-bound ZIF-8 crystals. However, cross-sectional SEM images revealed that most of the ZIF-8 crystals formed inside the polymer remained intact even after subjected to eight acid treatment cycles. As opposed to KAP-6-Zn-ZIF-8, the relative (110) intensity of KAP-2-Zn-ZIF-8 was reduced to 0% after subjected to similar acid treatment cycles as shown in FIG. 8B, suggesting ZIF-8 crystals formed mostly on the polymer surface. This strongly indicates that one can control the location of ZIF-8 crystals by simply adjusting the hydrolysis time.

Microstructure of KAP-6-Zn-ZIF-8

Figures 10A, 10B, 10C:
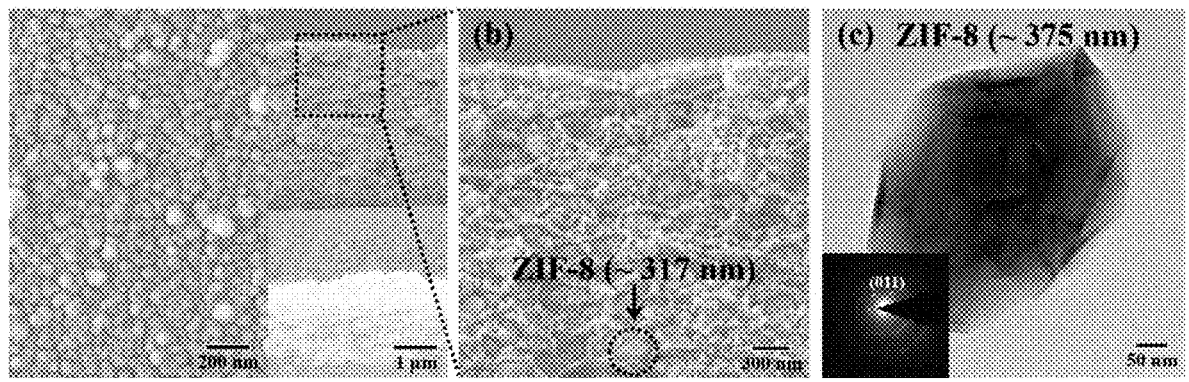
FIGS. 10A-10E are top and cross-sectional SEM images of KAP-6-Zn-ZIF-8 (FIG. 10A), a magnified view of the selected area in FIG. 9A (FIG. 104B), a cross-sectional TEM image of ZIF-8 crystals with electron diffraction pattern (FIG. 10C), and cross-sectional TEM images and electron diffraction patterns (inset) of KAP-6-Zn-ZIF-8 at location A (FIG. 10D) and at location B (FIG. 10E).
Figure 10D:
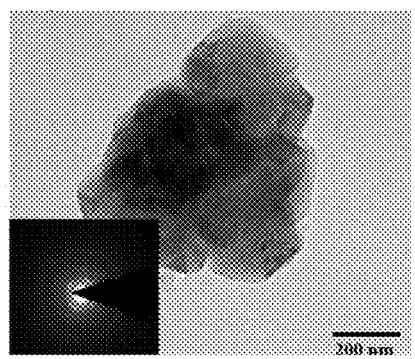
Figure 10E:
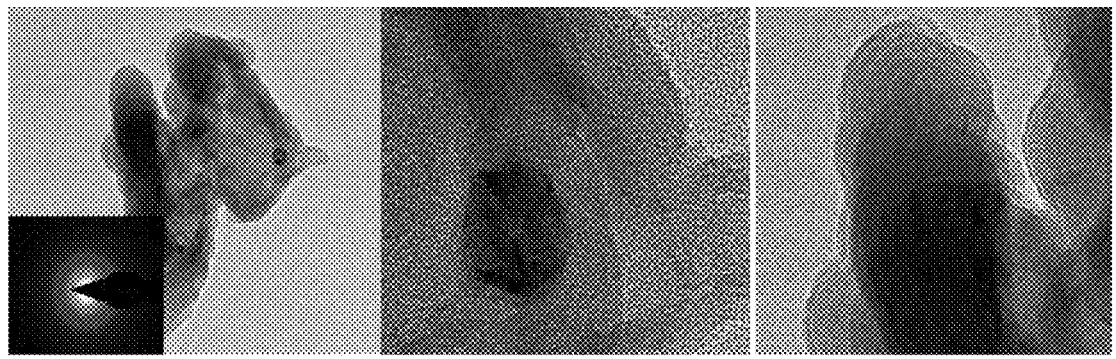

FIGS. 10A-10C show the microstructure of a representative KAP-6-Zn-ZIF-8 sample, showing that the size of the embedded ZIF-8 particles detected under SEM (FIG. 10A-10B) and TEM (FIG. 10C) was comparable. Although the observed particle shown in FIG. 10C appears to be a ZIF-8 single crystal, the inset electron diffraction suggests that the particle consists of several smaller ZIF-8 crystals, but of unknown sizes (FIG. 10D). TEM analysis also revealed the formation of some unknown amorphous phases inside the polymer (FIG. 10E). As best determined, in situ formation of ZIF-8 inside the polymer has never been reported previously. It is surmised that during the solvothermal reaction in a linker solution, ZIF-8 crystals formed not only at the polymer/solution interface (21) but also inside the polymer possibly due to the slow elution of free $Zn^{2+}$ ions from the polymer free volume, thereby allowing linker molecules to diffuse deep into and consequently crystallizing inside the modified layer. Inside the free volume spaces, several nuclei might form, resulting in ZIF-8 particles of several grains inside the polymer. It is notable that the ability to in situ form ZIF-8 nanoparticles inside polymer substrates bears a significant implication for the one-step synthesis of ZIF-8/polymer composite films and membranes.

Example 4

Formation of ZIF-67 and Mixed-Metal ZIFs Via PMMOF

In addition to ZIF-8, the PMMOF approach was also applied to synthesize thin films of ZIF-67 ($Co^{2+}$-substituted ZIF-8) and Zn/Co mixed-metal ZIF (hereafter, $Zn_xCo_y$-ZIF-8). A great deal of research has been undertaken to fine tune the properties (e.g., pore aperture, pore volume, functionality, etc.) of MOF crystals by mixed-metal (29-30) and mixed-linkers approaches (31-32). Versatility of the PMMOF process not only allows to entirely change the metal dopant (i.e., $Co^{2+}$) species, but also to tailor the composition of co-dopant species (i.e., $Zn^{2+}$ and $Co^{2+}$) in the polymer-modified layer, thereby enabling construction of monometallic and bimetallic ZIF films with rational control over metal compositions in the frameworks. ZIF-67 films are synthesized by simply replacing the metal dopant from $Zn^{2+}$ to $Co^{2+}$. $Zn_xCo_y$-ZIF-8 films were synthesized by doping the polymer substrates with a mixture of metal cations (i.e., $Zn^{2+}$ and $Co^{2+}$) of known composition. As a proof of concept, an aqueous mixture of zinc nitrate hexahydrate (50 mM) and cobalt nitrate hexahydrate (50 mM) were used during ion-exchange, forming equimolar mixture of the dopant species in the ZIF framework ($Zn_{0.5}Co_{0.5}$-ZIF-8). All samples were subjected to similar 6 min KOH treatment time and reaction conditions are maintained the same.

Figure 11A:
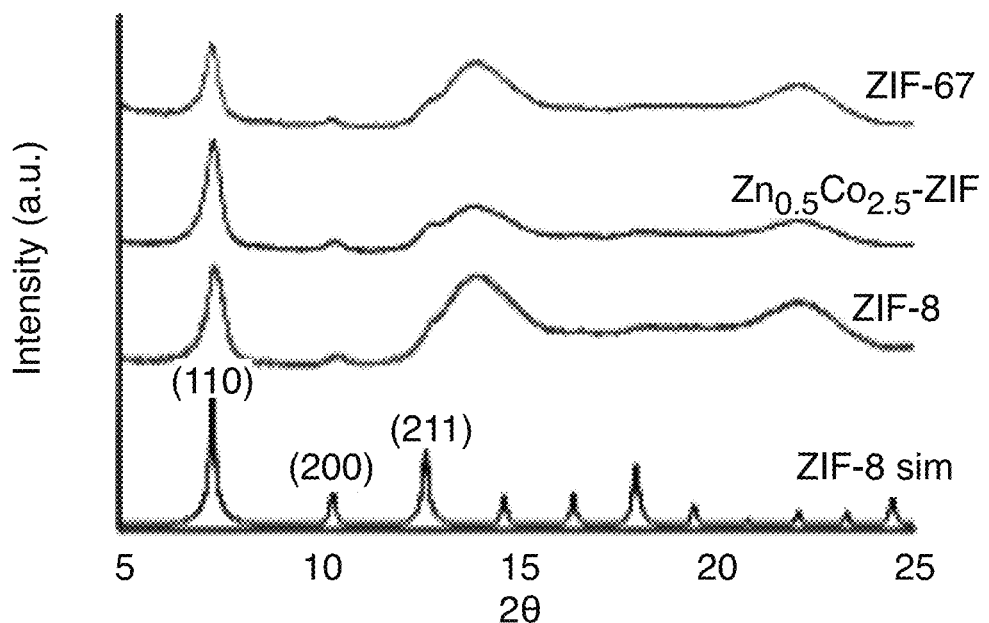
Figure 11B:
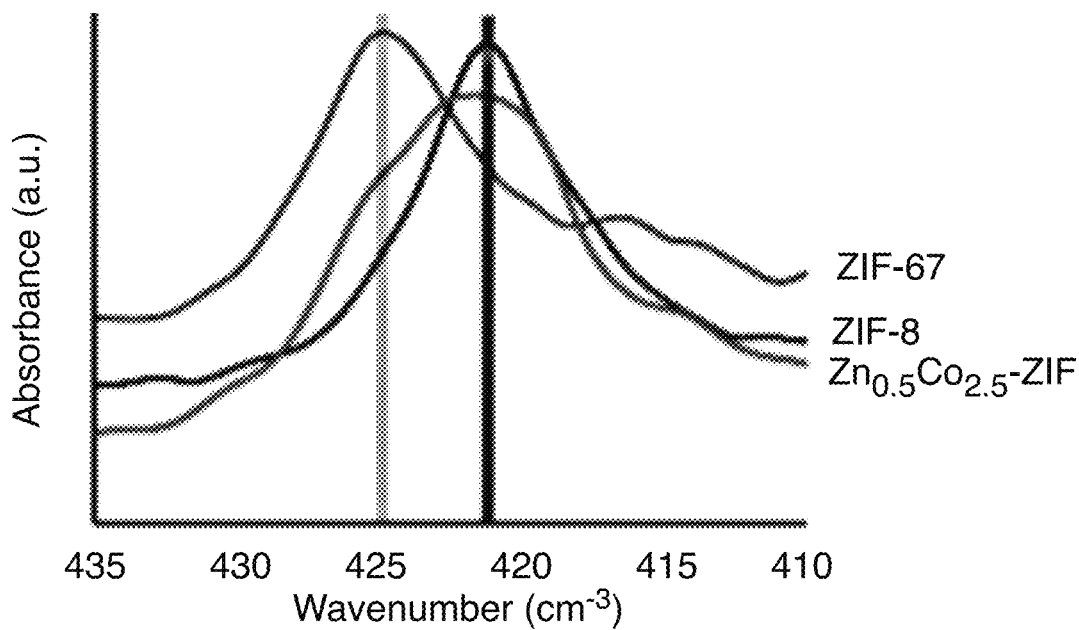

PXRD patterns in FIG. 11A confirmed the formation of phase-pure ZIF-8, $Zn_{0.5}Co_{0.5}$-ZIF-8, and ZIF-67 crystals. The resulting ZIF thin films are presented in FIGS. 11B-11I where several observations are made. Firstly, ZIF-8, $Zn_{0.5}Co_{0.5}$-ZIF-8, and ZIF-67 crystals were densely-packed yielding continuous films. Secondly, the films were made of grains with relatively narrow size distribution and the sizes of these grains appeared to be systematically increasing from ZIF-8>$Zn_{0.5}Co_{0.5}$-ZIF-8>ZIF-67 (40 nm vs. 155 nm vs. 271 nm). The difference in crystallite sizes is attributed to slower nucleation and crystal-growth kinetic upon incorporation of $Co^{2+}$ in the $Zn^{2+}$-doped substrates (30). For Zn/Co mixed-metal ZIF, interestingly, incorporation of $Co^{2+}$ and $Zn^{2+}$ into the framework can be monitored through direct optical observation of color change. To further confirm the incorporation of $Zn^{2+}$ and $Co^{2+}$ in ZIF frameworks, energy dispersive X-ray spectroscopy (EDX) line profile analysis were performed. EDX line scan analysis of $Zn_{0.5}Co_{0.5}$-ZIF-8 surfaces in FIG. 11D shows that $Zn^{2+}$ and $Co^{2+}$ were uniformly distributed throughout. Relative amount between $Zn^{2+}$ and $Co^{2+}$ was close to unity and was found to be consistent with those of co-doped polymer substrates (FIGS. 11C, 11E-11F).

Additionally, metal-to-nitrogen absorption bands of $Zn_{0.5}Co_{0.5}$-ZIF-8 became broader and blue-shifted upon incorporation of $Co^{2+}$ into the ZIF-8 frameworks, which agrees with that previously reported (33). $Zn_{0.5}Co_{0.5}$-ZIF-8 (Zn/Co mixed-metal ZIF) consisting of more rigid Co—N (i.e., stiffer) and less rigid Zn—N alter metal-to-nitrogen stretching frequency, thus leading to this blue-shift (34). An ability to control dopants and their compositions in polymer substrates present an unprecedented opportunity to fabricate important monometallic families of ZIFs and bimetallic ZIF films for a variety of applications. Finally, site-selective interfacial reaction allows for construction of one and/or multiple types of ZIF films grown on specific locations on polymer substrates. When ion exchanged with $Co^{2+}$ on one side and $Zn^{2+}$ on the other side, ZIF-67 and ZIF-8 films were formed on different sides (FIG. 11J) (Janus MOF films).

Example 5

Figure 12A:
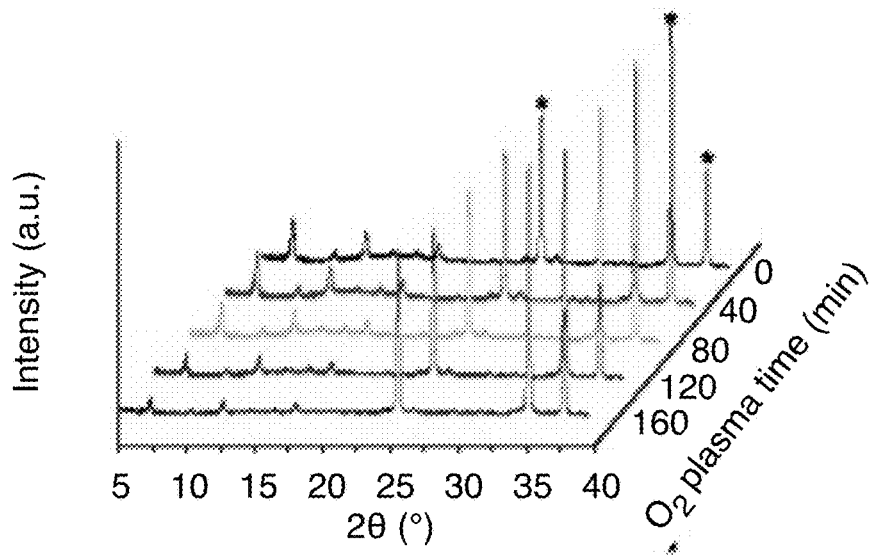
FIGS. 12A-12D show results of methanol and ethanol based Hmim treatment of PI/ZIF-8 as a function of oxygen etching plasma time.
Figure 12B:
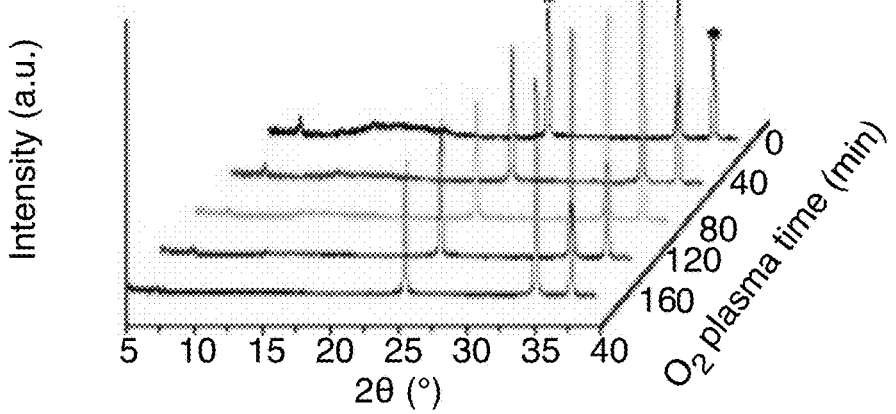
Figure 12C:
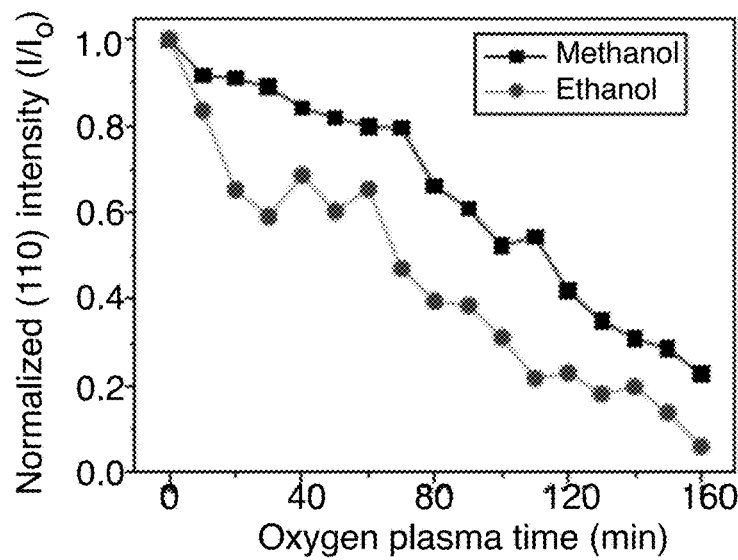
Figure 12D:
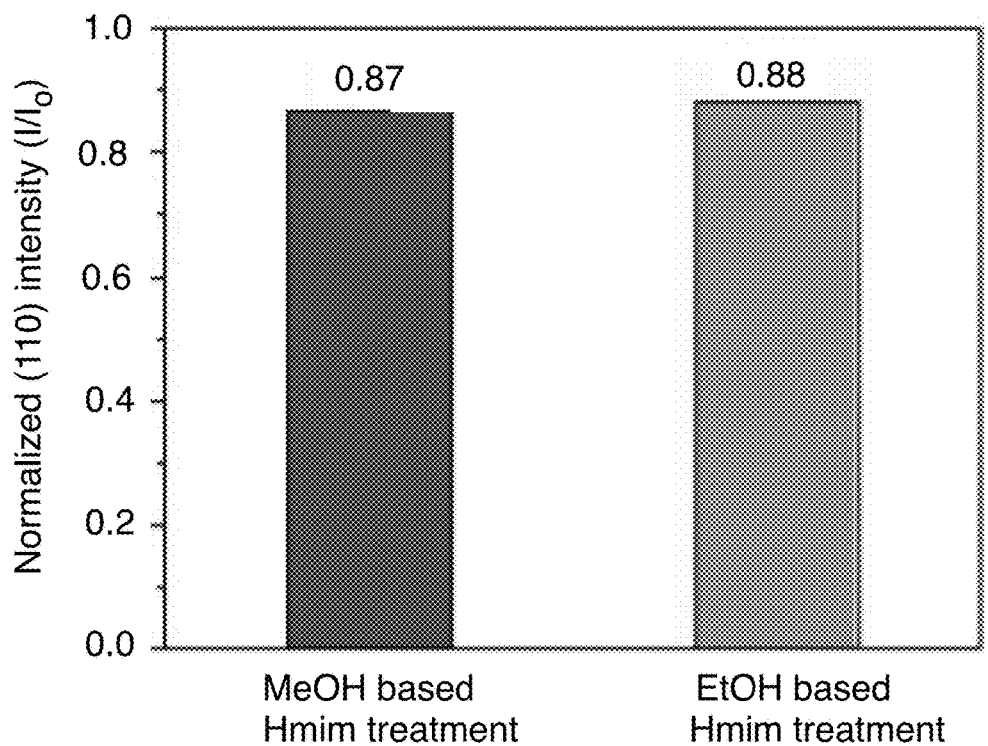

Structure Control and Characterization of 6FDA-DAM/ZIF-8 MMMS by PMMOF Distribution of ZIF-8 Particles in 6FDA-DAM/ZIF-8 Polymer Matrix The distribution of in situ formed ZIF-8 nanoparticles is influenced by the diffusion of organic linkers (i.e., Hmim) into a polymer matrix. The diffusion of Hmim through the polymer can be controlled by the type of solvents: size of solvents and affinity of solvents with the polymer. To characterize the distribution of ZIF-8, an oxygen plasma etching was conducted. The XRD peaks of two PI/ZIF-8 samples, one Hmim-treated in methanol (named PI/ZIF-8_MeOH) and the other in ethanol (named PI/ZIF-8_EtOH), were taken as a function of oxygen plasma etching time (FIGS. 12A-12B.). FIG. 12C presents the relative (110) peak intensities of the samples normalized by those of the as-prepared samples. The linear decrease of the (110) peak intensity likely indicates the uniform distribution of ZIF-8 nanoparticles in the polymer. For the PI/ZIF-8-MeOH, there observed a quite linear decline of the relative (110) peak intensity (FIG. 12C). On the other hand, in the case of the PI/ZIF-8_EtOH, the relative (110) intensity was sharply dropped for 20 min of initial oxygen plasma etching. The precipitous decrease of the (110) intensity of the PI/ZIF-8_EtOH was possibly due to the relatively high concentration of ZIF-8 near the surface of the sample. It should be mentioned that both samples showed comparable changes in their (110) peak intensities after the removal of surface bonded ZIF-8 particles by the acid treatment, indicating that the sharp decrease upon the etching is not owing to the decomposition of surface grown ZIF-8 (FIG. 12D). Since ethanol is bulkier and less polar compared to methanol, the diffusion of Hmim in ethanol inside the polymer is restrained as compared with that in methanol, thereby forming more crystals near the surface.

Shape and Size of ZIF-8 Particles in 6FDA-DAM/ZIF-8 Polymer Matrix

Figure 13:
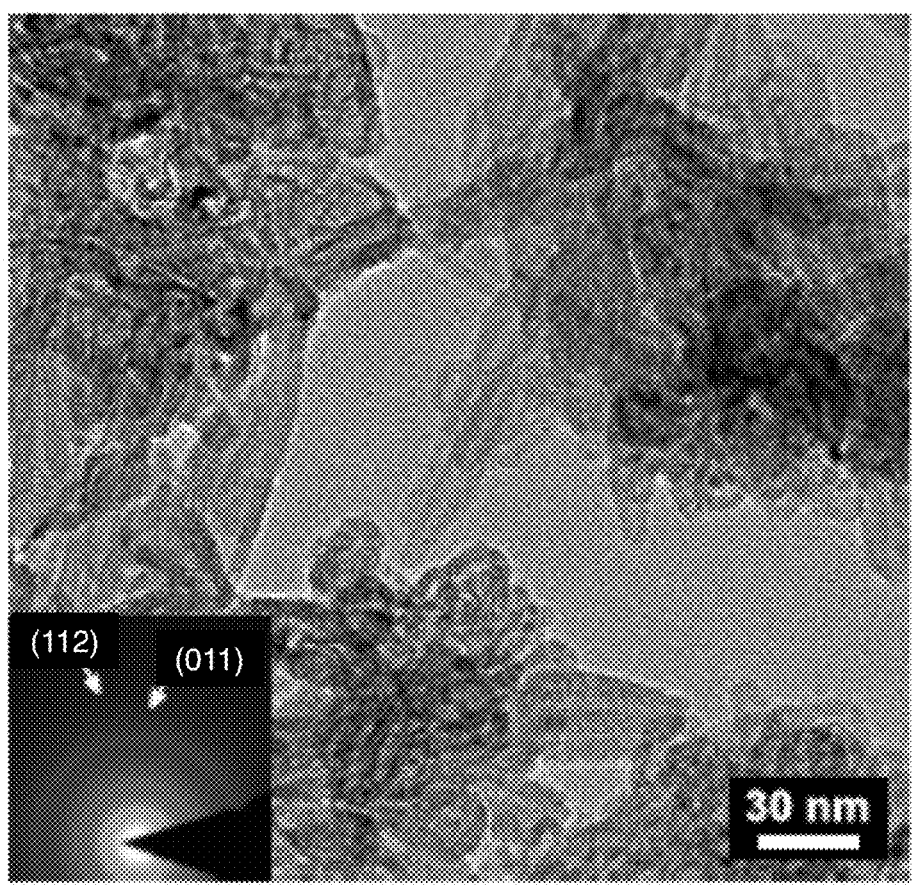
FIG. 13 is a TEM image of in-situ grown ZIF-8 nanoparticles in PI/ZIF-8 and its selected-area electron diffraction (SAED) pattern (bottom left).

The shape and size of ZIF-8 nanoparticles within a polymer was confirmed by the TEM images of a PUZIF-8 sample (FIG. 13). The morphology of the in situ grown ZIF-8 crystals was an anisotropic rod-like structure with a high aspect ratio unlike that of the surface grown ZIF-8 (FIG. 4B). It is noteworthy that rod-shaped ZIF-8 nanoparticles have been reported in few previous work (35). Interestingly, the (110) peak intensity of XRD patterns was notably decreased relative to the (112) peak intensity after removing the surface grown ZIF-8 crystals (FIG. 4F). To quantify, crystallographic preferred orientation (CPO) was determined by taking the ratio of the (112)/(110) of the samples normalized by that of a randomly oriented sample (36). The estimated CPO(112)/(110) of the PI/ZIF-8 after removing surface grown ZIF-8 (~2.85) was 1.65 times greater than that of the PI/ZIF-8 with the surface grown ZIF-8 (~1.73) (Table 2).

TABLE 2

CPO$_{(112)/(110)}$ of PMMOF processed MMMs

| Sample | CPO$_{(112)/(110)}$ |
| --- | --- |
| PI/ZIF-8 ZN(8) | 2.60 |
| PI/ZIF-8 ZN(16) | 1.81 |
| PI/ZIF-8 ZN(16) after surface acid treatment | 2.85 |
| PI/ZIF-8 ZN(24) | 2.17 |
| PI/ZIF-8 ZN(32) | 2.43 |
| PI/ZIF-8 ZN(40) | 2.51 |

There were similar observations that an anisotropic shaped ZIF-8 showed a relatively high CPO(112)/(110) (35). The previous study by Yang et al. (35) showed the shape of ZIF-8 was controllable by using a shape-inducing agent, cetyltrimethylammonium bromide (CTAB), which adsorbed preferentially onto certain surface facets of ZIF-8, thereby decreasing the crystal growth of those facets.

Anisotropic nano-rod- and interpenetrated twin-shaped ZIF-8 crystals showed relatively low (110) peak intensity, resulting in the higher CPO(112)/(110) than that of other shapes, 13 consistent with our observation. Also, despite agglomeration, the size of the ZIF-8 crystals in a polymer was less than ~100 nm significantly smaller than that of ZIF-8 formed on the surface. These differences in the shape and size of ZIF-8 crystals are probably because the growth of ZIF-8 inside the polymer occurs in confined spaces while the interfacial growth of ZIF-8 happens in unconfined spaces.

Concentration of ZIF-8 Particles in 6FDA-DAM/ZIF-8 Polymer Matrix

Figure 14:
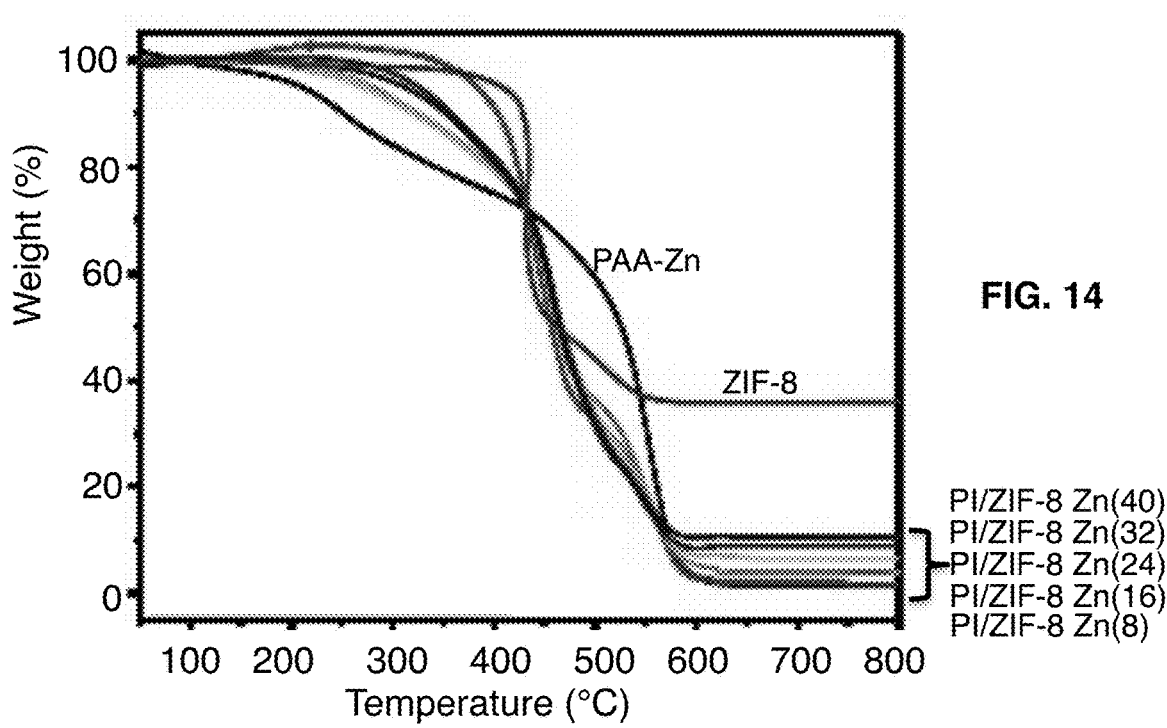
FIG. 14 is a TGA thermogram of PAA-ZN, ZIF-8 and PI/ZIF-8 with different zinc concentrations.

The concentration of in situ grown ZIF-8 in a polymer was controlled by varying the concentration of zinc in an ion exchange solution since the excess Zn ions are the main source for ZIF-8 nanoparticles forming in a polymer as mentioned earlier. It is noted that the concentration of Zn ion coordinated to polymer is expected independent of the concentration of a zinc solution, rather depending on the degree of deimidization. The zinc content in the solution was varied at 8, 16, 24, 32, and 40 mmol in 40 ml water and the zinc concentration was denoted as Zn (mmol). As the zinc concentration increased, TGA analysis presented in FIG. 14 7 showed an increase in ZnO residues upon thermal oxidization, indicating that the concentration of ZIF-8 increased. The calculated percentages of ZIF-8 within a polymer are represented in Table 3.

TABLE 3

Weight and volume percentages of ZIF-8 in PMMOF processed MMMs

| Sample | Weight percentage (wt %) | Volume percentage (vol %) |
| --- | --- | --- |
| PI/ZIF-8 ZN(8) | 4.2 | 5.9 |
| PI/ZIF-8 ZN(16) | 9.2 | 12.8 |
| PI/ZIF-8 ZN(24) | 15.9 | 21.4 |
| PI/ZIF-8 ZN(32) | 20.3 | 26.8 |
| PI/ZIF-8 ZN(40) | 25.5 | 32.9 |

Quantification of in situ grown ZIF-8 nanoparticles in a polymer is described in Example 1. High ZIF-8 content in a polymer matrix can be obtained due to expanded volume of the polymer upon the hydrolysis, consequently increasing the uptake of metal and ligand sources during the PMMOF process. The bulk volume of PAA-Zn increased 7.7±2.0% and 14.3±1.9% when swollen in water and in methanol, respectively (Table 4).

TABLE 4

Volume swelling of PAA-Zn in water and methanol

| Solvent | Volume swelling (%) |
| --- | --- |
| Water | 7.7 ± 2.0 |
| Methanol | 14.3 ± 1.9 |

Example 6

$C_3H_6/C_3H_8$ Separation Performances

Figure 15A:
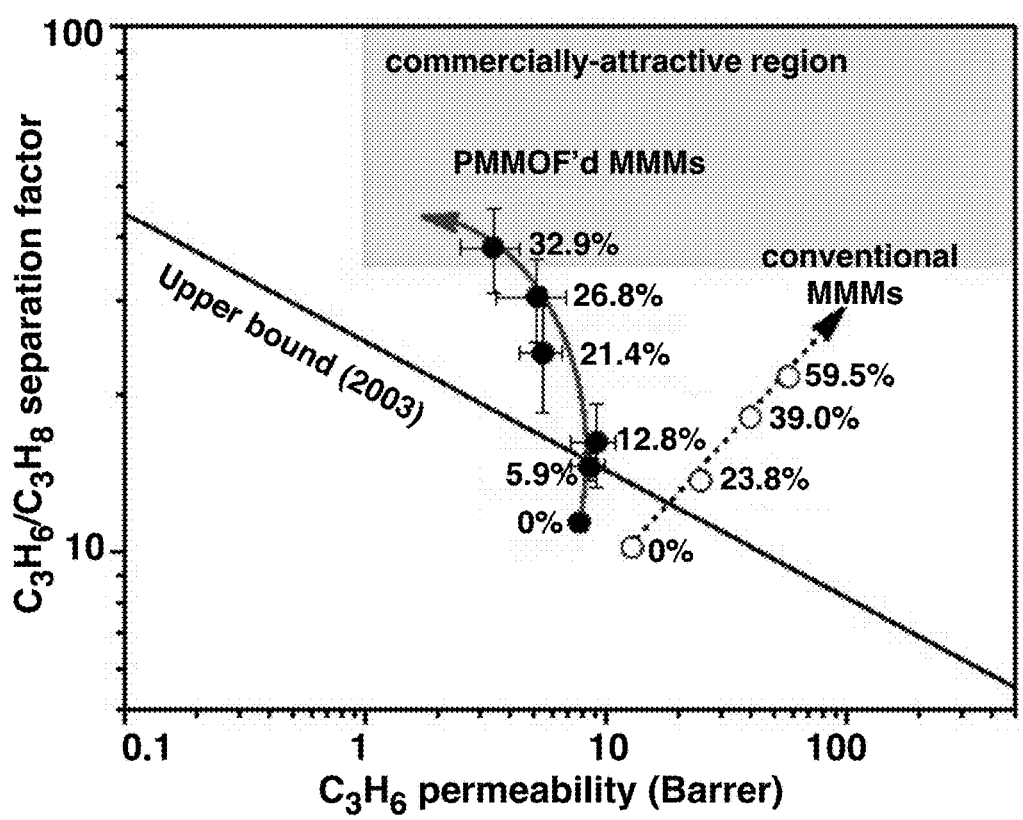
FIGS. 15A-15B show the gas transport results and separation performance of 6FDA-DAM and/or PMMOF processed mixed-matrix membranes for $C_3H_6/C_3H_8$ separation.

The $C_3H_6/C_3H_8$ separation performances of the PI/ZIF-8 mixed-matrix membranes prepared by the PMMOF (PM-MOFed MMMs) were investigated and compared with conventional mixed-matrix membrane counterparts prepared by blending ZIF-8 nanoparticles with polymer. The conventional mixed-matrix membranes exhibited an increase in the $C_3H_6/C_3H_8$ separation factor as well as the $C_3H_6$ permeability as the ZIF-8 loading in the polymer increased (FIG. 15A). The PMMOF processed mixed-matrix membranes, surprisingly, showed a slight decrease in the $C_3H_6$ permeability with a more dramatic increase in the $C_3H_6/C_3H_8$ separation factor of up to 38.0±7.1 (FIG. 15A 8a). The $C_3H_6$ permeability remained unchanged at the ZIF-8 particle loading increasing up to ~13 vol % and then decreased as the ZIF-8 loading further increased. The decreasing permeability as increasing ZIF-8 loading is ascribed possibly to the decrease in the permeability of the continuous polymer phase with increasing ZIF-8 loading.

This is likely due to a decrease in the polymer free volume (i.e., densification), leading to a decrease in the permeability of the PMMOF processed mixed-matrix membranes with increasing ZIF-8 loading. It is not unreasonable to assume that the in situ growth of ZIF-8 in the polymer free volume enlarged by hydrolysis and swelling might decrease the polymer free volume.

Figure 15B:
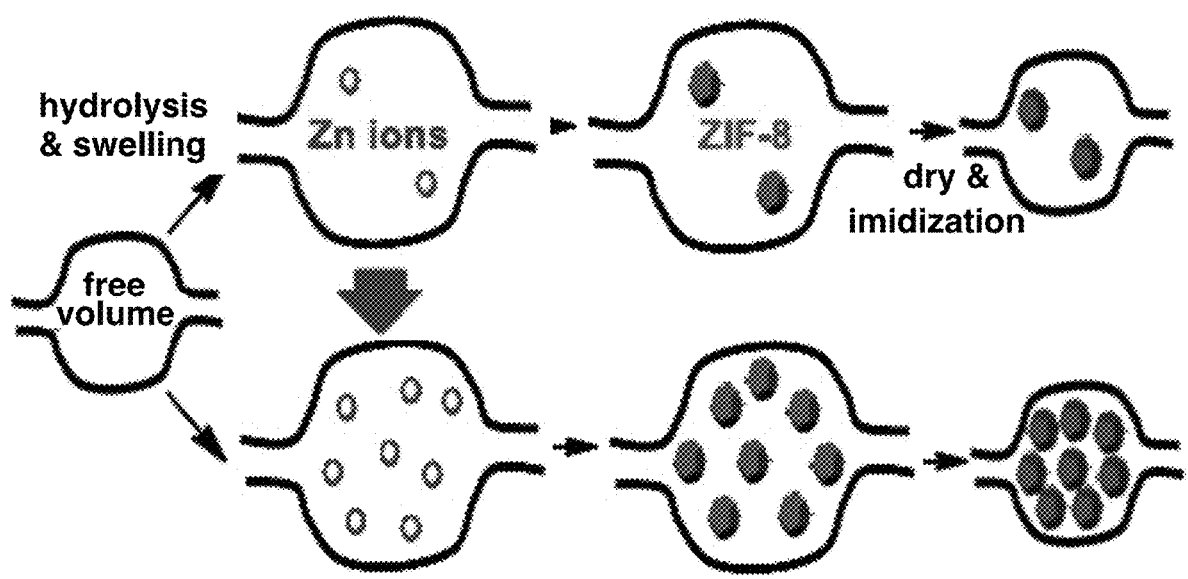

To qualitatively estimate the densification effect of the polymer, the $C_3H_6$ and $C_3H_8$ permeabilities of the polymer in the corresponding PMMOF processed MMMs were evaluated using Maxwell equation (37). Maxwell equation has been widely used for evaluating the gas separation performances of mixed-matrix membranes due to its simplicity and accuracy. While both of the $C_3H_6$ permeability and the $C_3H_6/C_3H_8$ separation factor of ideal MMMs were continuously enhanced with increasing ZIF-8 loading as observed in conventional MMMs, the predicted $C_3H_6/C_3H_8$ separation of polymer phases showed a decreasing trend in the $C_3H_6$ permeability and an increasing trend in the $C_3H_6/C_3H_8$ separation factor, following the polymeric upper bound (FIG. 15B). The estimated $C_3H_6/C_3H_8$ separation performance of the polymer slightly outperforms the upper bound likely due to the uncertainty of Maxwell model at high ZIF-8 loadings. The Maxwell model is valid at loadings less than 20 vol %.

For $C_3H_6/C_3H_8$ separation using a membrane technology, a higher separation factor is more demanding and desired than a higher permeability (38-39). The PMMOF processed PI/ZIF-8 mixed-matrix membranes represented much higher $C_3H_6/C_3H_8$ separation factor than that of the conventionally prepared PI/ZIF-8 mixed-matrix membranes even at the lower ZIF-8 concentration. As shown in FIG. 15A, these high $C_3H_6/C_3H_8$ separation factor and moderate $C_3H_8$ permeability marginally satisfied the commercially-attractive region in the Robeson plot at the ZIF-8 concentration of 32.9 vol % (40). Furthermore, the PMMOF processed mixed-matrix membranes show the second highest $C_3H_6/C_3H_8$ separation factor among the reported polymer-based mixed-matrix membranes (41). Despite the compromise in the permeability, the exceptionally high separation factor of the PMMOF processed mixed-matrix membranes as compared to conventional mixed-matrix membranes is likely due to not only better adhesion and enhanced distribution of ZIF-8 in a polymer matrix, but also densification of polymer matrix induced by the in situ growth of ZIF-8 nanoparticles in polymer free volume.

Example 7

Applicability of PMMOF to Other MOFs

Figures 16A, 16B:
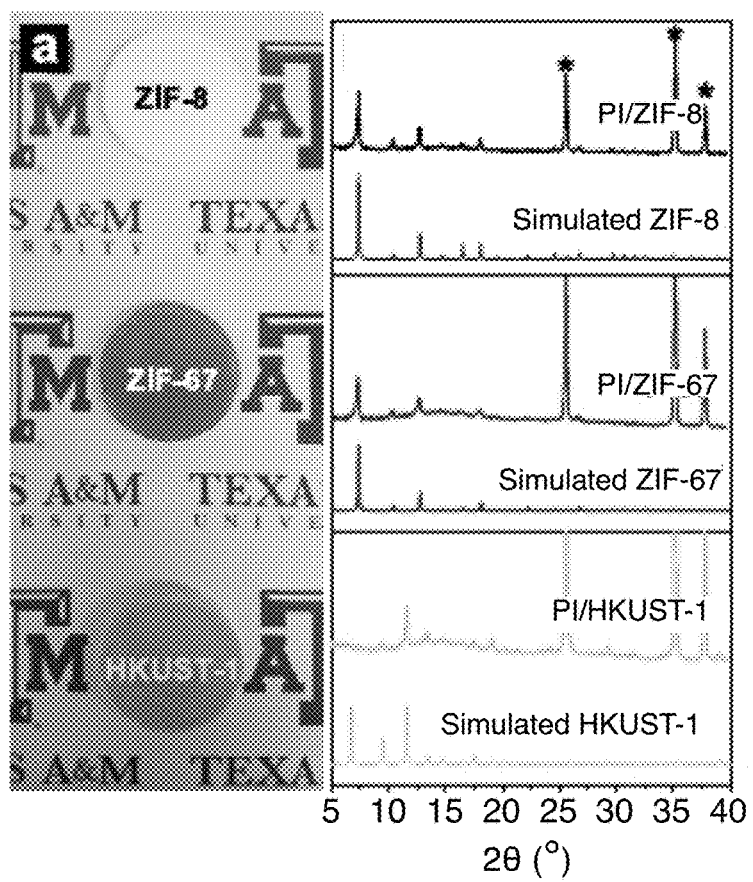
FIGS. 16A-16B show photographs and XRD patterns of PMMOF processed mixed-matrix membranes.
Figure 18A:
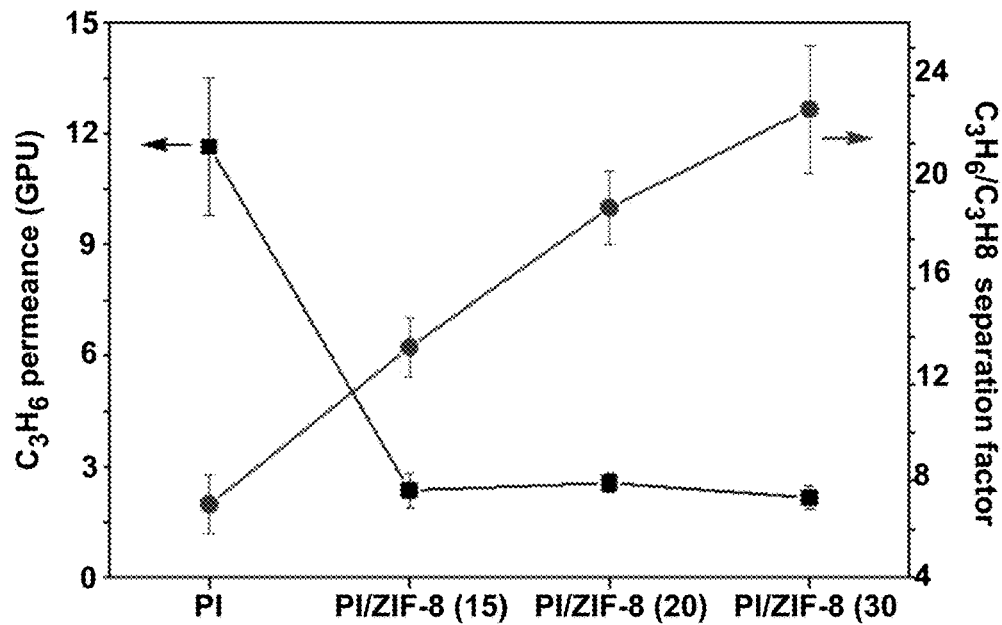
FIGS. 18A-18B show the effect of ZIF-8 loading on C3 separation performance (FIG. 18A) and $C_3H_6$ permeance and C3 separation factor of single-strand PI/ZIF-8 MMHFM modules in comparison with those of previously reported HFMs (FIG. 18B).
Figure 18B:
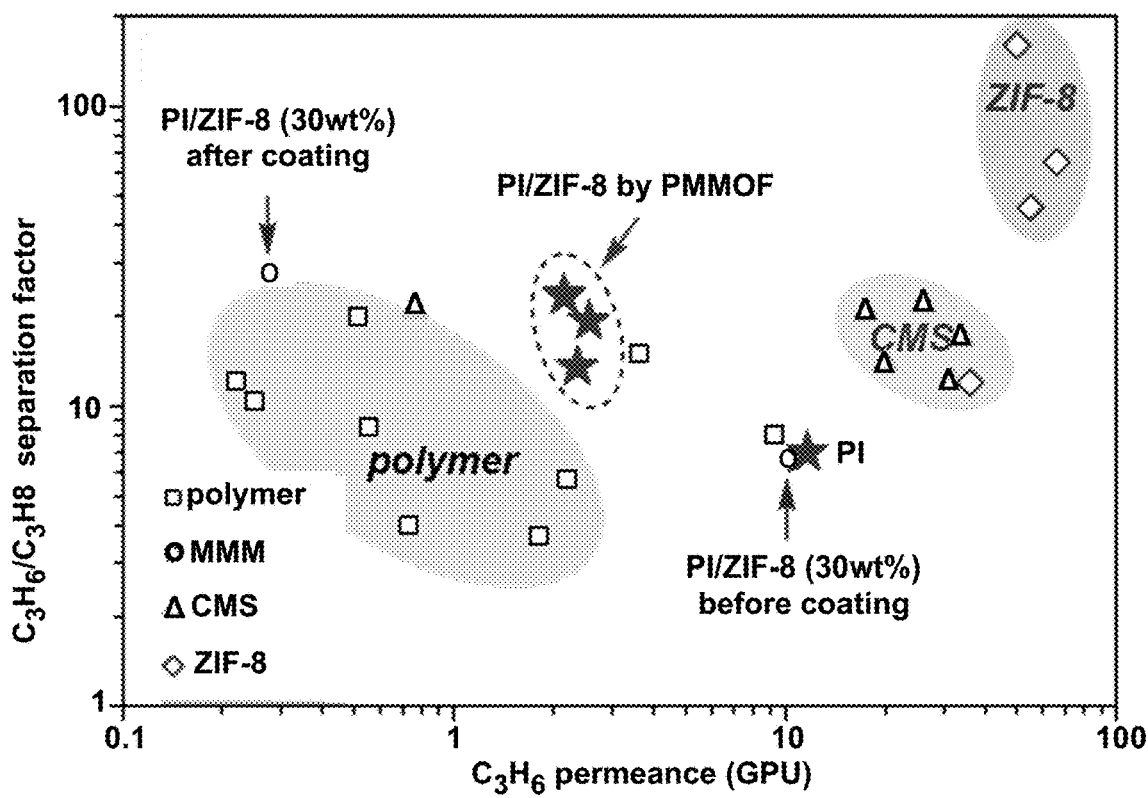

General applicability of the PMMOF was tested using other MOFs including ZIF-67 and HKUST-1. As shown in FIG. 16A, depending on the type of MOFs, the colors of the PMMOFed mixed-matrix membranes were varied; white for PI/ZIF-8, violet for PI/ZIF-67, and turquoise for PI/HKUST-1 mixed-matrix membranes. The crystal phases of the in situ grown MOFs inside polymers well-matched with the corresponding simulated patterns, supporting the general applicability of the PMMOF (FIG. 16B). Note that photographs and XRD patterns were taken after removing surface-bound MOFs by acid treatment. The PMMOF process is, therefore, expected to enable facile formation of a myriad number of MOF/polymer composite films/membranes by combining various MOFs and polyimide-based-polymers. This makes a stark contrast in that conventionally prepared MOF/polymer composite films have been limited to certain MOFs and polymer combinations often due to the poor compatibility between certain polymers and MOFs. (42) Not only are MOF polymer composite films prepared by the PMMOF very useful for separation applications, but also polymer composites with a various kind of MOFs with different functionalities can also be applied in the diverse areas such as gas/liquid adsorption, (43) capacitive sensors, (45) and proton exchange membranes for fuel cell (45).

Example 8

PMMOF Transformation of a Polymer HFM Modules to PI/ZIF-8 MMFHM Module

A thin 6FDA-DAM polyimide (PI) layer was dip-coated on a commercial polyethersulfone (PES) hollow fiber membrane, several of which were then assembled into a module with both of the ends open (FIGS. 1A-1C). PES HFMs were selected as supports due to their low material cost (~20 USD/kg), mechanical, chemical (mostly inert to the PMMOF), and thermal stability ($T_g$ of ~220° C.) as well as their compatibility with fluorinated polyimides. Ethyl acetate was chosen as a solvent since it dissolves 6FDA-DAM while PES HFMs were intact in ethyl acetate. The PI-coated HFMs were assembled into a module by sealing both ends with epoxy (FIG. 1D).

During the PMMOF process the hydrolysis reaction must be properly controlled. The hydrolysis reaction partially deimidizes a PI layer to form a poly(amic acid) sodium salt (PAA-Na) layer. This hydrolysis step is essential to provide environments inside the polymer to enable accommodation of MOF precursors and eventually in-situ MOF formation inside polymer. Since the PI coating layer on a PES HFM was much thinner (~0.75 μm) than that on a flat alumina disk (~7 μm), the hydrolysis conditions must be much milder than required to form PMMOF processed mixed-matrix membranes.

Sufficient soaking by a zinc solution during the ion-exchange step is required. Due to the nature of the module, air bubbles were trapped within the module, thereby limiting saturation by the solution. As such, air bubbles were removed by evacuating one side of the HFM module under vacuum while solutions were supplied to the other side.

During the ligand treatment step where ZIF-8 forms in polymer free volume (PAA/ZIF-8), the polymer HFMs were most swelled, thereby causing damages to the skin layers in the limited space of the module. It was possible to alleviate these damages by maintaining the packing density of the hollow fiber module at <30%. The last step was to thermally imidize the PAA to the PI, stabilizing the gas separation performance of the membrane. During this thermal imidization step, an epoxy with high thermal resistance was used to minimize the thermal expansion and degradation of epoxy.

Example 9

$C_3H_6/C_3H_8$ Separation Performance of the PI/ZIF-8 MMFHM Modules

The C3 separation performances of the PI/ZIF-8 MMHFM modules were comparable with those of corresponding previously reported single-fiber MMHFMs. For example, the $C_3H_6$ permeances of the PI/ZIF-8 (20) MMHFM modules were 2.17 GPU (single fiber) and ~2.55 GPU (module). The separation factors were ~20 (single fiber) and ~19.3 (module) (23). It is contemplated that PMMOF is applicable to hollow fibers whether they are in a module or as individual fibers.

The effect of ZIF-8 contents on C3 separation performance was investigated. When the loading percentages of ZIF-8 in the PI/ZIF-8 MMHFMs increased, the C3 separation factor increased because of the molecular sieving effect of ZIF-8 (FIG. 3A). ZIF-8 loading had a little effect on the $C_3H_6$ permeances of the PI/ZIF-8 MMHFMs. Upon the PMMOF, the $C_3H_6$ permeance was significantly reduced about five-fold (FIG. 3A). This noticeable permeance reduction likely was due to the polymer densification upon the PMMOF. Nevertheless, the separation factor of the PI/ZIF-8 MMHFMs was significantly increased at the higher ZIF-8 loadings.

The C3 separation performances of the single-strand PI/ZIF-8 MMHFM modules were compared with previously reported other hollow fiber membranes including polymer, CMS, ZIF-8, and PI/ZIF-8 MMHFMs prepared by conventional blending methods. Despite the potential of MMHFMs, there has been only one prior report on MMHFMs for C3 separation. Even though the PI/ZIF-8 MMHFMs prepared by a blending method showed C3 separation capability, the separation factor of the as-spun MMHFMs was lower than that of the polymer HFMs due to defects. Therefore, additional coating steps were necessary to improve the separation factor, significantly sacrificing propylene permeance. The defects on MMHFMs were generally formed upon a spinning process due to the complicated parameters associated with spinning a filler suspended dope solution.

Unlike the PI/ZIF-8 MMHFMs made by conventional blending, the MMHFMs by the PMMOF showed more improved C3 separation performances even without additional coatings (FIG. 3B). When additional PDMS coating was applied to the PI/ZIF-8 MMHFMs prepared by the PMMOF, there were no further improvements of the C3 separation factor, indicating the absence of major defects. Decoupling of spinning step and MMM formation step in the PMMOF effectively suppressed defect formations.

The following references are cited herein:
1. Sanders et al., Polymer, 54(18):4729-4761, 2013.
2. Ghosh et al., Ind Eng Chem Res, 32(10):2390-2399, 1933.
3. Kwon et al., J Am Chem Soc, 137(38):12304-12311, 2015
4. Lee et al., Angew Chem Int Edit, 57(1):156-161, 2018.
5. Pimentel et al., Chemsuschem, 7(12):3202-3240, 2014.
6. Dong et al., J Mater Chem A, 1(15):4610-4630, 2013.
7. Hamid et al., Korean J Chem Eng, 35(8):1577-1600.
8. Zhang et al., J Phys Chem Lett, 6(19):3841-3849, 2015.
9. Tsuruoka et al., Cryst Growth Des, 16(5):2472-2476, 2016.
10. Marti et al., Acs Appl Mater Inter, 10(29):24784-24790, 2018.
11. Burns et al., J Membrane Sci, 211(2):299-309, 2003.
12. Zhang, C., Zeolitic Imidazolate Framework (ZIF)-Based Membranes and Sorbents for Advanced Olefin/Paraffin Separations. Georgia Institute of Technology, 2014.
13. Woo et al. J. Membr. Sci., 498:125-134, 2016.
14. Mulder, J., Basic Principles of Membrane Technology, Springer Science &
Business Media, 2012.
15. Kwon, H. T. and Jeong, H.-K., J. Am. Chem. Soc., 135:10763-10768.
16. Yu et al., J Polym Sci Pol Chem, 54(11):1593-1602, 2016.
17. Xu et al., J Wuhan Univ Technol, 31(5):1137-1143, 2016.
18. Kim et al., Colloid Surface A, 321(1-3):292-296, 2008.
19. Wind et al., Ind Eng Chem Res, 41(24):6139-6148, 2002.
20. Ba et al, Journal of Membrane Science, 363(1-2):140-148, 2010.
21. Taubert et al., Polymer, 44(6):1881-1892, 2003
22. Wu et al., Rsc Adv, 5(100):82127-82137, 2015.
23. Lively et al., J Membrane Sci, 423:302-313, 2012.
24. Huang et al., J. Polym. Int., 52:1064-1069, 2003.
25. Yang et al., J. Phys. Chem. B, 113:9694-9701, 2009.
26. Akamatsu et al., Chem. Mater., 15:2488-2491, 2003.
27. Wang et al., RSC Adv., 5:87496-87503, 2015.
28. Pradhan et al., J. Phys. Chem. C, 113:15788-15791, 2009.
29. Tsuruoka et al., J. Solid State Chem., 253:43-46, 2017.
30. Wang et al., Chem. Commun., 52:12578-12581, 2016.
31. Eum et al., J. Am. Chem Soc., 137:4191-4197, 2015.
32. Huang et al., Inorg. Chem. Commun., 46:9-12, 2014.
33. Hillman et al., J. Mater. Chem. A, 5:6090-6099, 2017.
34. Kwon et al., J. Am. Chem. Soc., 137:12304-12311, 2015.
35. Yang et al., Chem Mater, 30(10):3467-3473, 2018.
36. Hou et al., Chemphyschem, 14(1):140-144, 2013.
37. Pal, R., J Colloid Interf Sci, 317(1):191-198, 2008.
38. Koros et al., Aiche J, 58(9):2624-2633, 2012.
39. I. BCS, O., Materials for Separation Technologies: Energy and Emission Reduction Opportunities, US Department of Energy: Energy Efficiency and Renewable Energy, 2005.
40. Craig Colling, G. H. and Bartels, J., Process Using Solid Perm-Selective Membranes in Multiple Groups for Simultaneous Recovery of Specified Products from a Fluid Mixture, 2002.
41. Ma et al., ACS Applied Nano Materials, 1(7):3541-3547, 2018.
42. Semino et al., Chemical Science, 9(2):315-324, 2018.
43. Ahmed et al., Materials Today, 17(3):136-146, 2014.
44. Sachdeva et al., ACS Sensors, 1(10):1188-1192, 2016.
45. Liang et al., Chemical Science, 4(3):983-992, 2013.

What is claimed is:

1. An in situ method for fabricating a mixed-matrix membrane, comprising:
    coating a polyimide polymer onto at least one support;
    hydrolyzing the polyimide polymer with a base to produce a poly(amic acid)-salt film;
    exchanging salt ions in the poly(amic acid)-salt film with metal ions in an aqueous metal salt solution to produce a poly(amic acid)-metal salt film;
    treating the poly(amic acid)-metal salt film with an organic linker to produce metal-organic framework nanoparticles in situ; and
    imidizing the treated poly(amic acid)-metal salt film to produce a polyimide/metal-organic framework mixed-matrix membrane.

2. The method of claim 1, wherein the polyimide polymer is (4,4-(Hexafluoroisopropylidene)diphthalic anhydride-2,4,6-trimethyl-1,3-phenylene diamine (6FDA-DAM), pyromellitic dianhydrides oxidianiline (PMDA-ODA), 3,3-4,4-benzophenone tetracarboxylic dianhydride diaminophenylindane (BTDA-DAPI).

3. The method of claim 1, wherein the support is at least one hollow fiber or at least one hollow fiber membrane, a fiber, a flat sheet, or a film.

4. The method of claim 1, wherein the base is sodium formate, sodium hydroxide, potassium hydroxide, barium hydroxide, cesium hydroxide, strontium hydroxide, calcium hydroxide, lithium hydroxide, or rubidium hydroxide.

5. The method of claim 1, wherein the aqueous metal salt solution is a nitrate, acetate, sulfate or chloride salt solution of zinc, cobalt, magnesium, manganese, iron, nickel, copper, or cadmium or a combination thereof.

6. The method of claim 1, wherein the organic linker is imidazole, 2-methylimidazole, 2-ethylimidazole, 2-nitroimidazole, benzimidazole, 6-nitrobenzimidazole, or purine.

7. The method of claim 6, wherein the organic linker is 2-methylimidazole (Hmim).

8. The method of claim 1, wherein the hydrolyzing step opens imide rings in the polyimide polymer to produce a poly(amic acid) sodium salt.

9. The method of claim 8, wherein the exchanging step exchanges sodium ions in the poly(amic acid) sodium salt with zinc ions to form a poly(amic acid) zinc salt film.

10. The method of claim 9, wherein the hydrolyzed polyimide polymer has an increase in free volume and hydrophilicity such that diffusion of the zinc ions inside the polymer is increased.

11. The method of claim 9, wherein the treating step produces zeolitic imidazolate framework nanoparticles inside the poly(amic acid) zinc salt film to form a poly(amic acid)-Zn/zeolitic imidazolate framework.

12. The method of claim 11, wherein the zeolitic imidazolate framework is ZIF-8 or ZIF-67.

13. The method of claim 11, wherein the imidizing step produces a polyimide/zeolitic imidazolate framework mixed-matrix membrane.

14. The method of claim 13, wherein the polyimidazole/zeolitic imidazolate framework mixed-matrix membrane is polyimide/ZIF-8.

15. The method of claim 1, wherein the support is a plurality of hollow fiber membranes, the coating step comprising:
coating a layer of the polyimide polymer onto each of the plurality of hollow fiber membranes to produce a plurality of polyimide polymer hollow fiber membranes; and
assembling the plurality of polyimide polymer hollow fiber membranes into a module.

16. A mixed-matrix membrane hollow fiber module fabricated by the method of claim 15.

17. The mixed-matrix membrane hollow fiber module of claim 16 that is a 6FDA-DAM/ZIF-8 mixed-matrix hollow fiber membrane module.

18. A method for separating a propylene/propane gas mixture, comprising:
flowing the propylene/propane gas mixture through the mixed-matrix membrane hollow fiber module of claim 16.

19. A mixed-matrix membrane fabricated by the method of claim 1.

20. The mixed-matrix membrane of claim 19, wherein the mixed-matrix membrane is doped with at least one of zinc, cobalt, magnesium, manganese, iron, nickel, copper, or cadmium.

21. The mixed-matrix membrane of claim 20 that is a polyimide/ZIF-8 mixed-matrix membrane doped with zinc or a polyimide/ZIF-67 mixed-matrix membrane doped with cobalt.

22. The mixed-matrix membrane of claim 19, said mixed-matrix membrane fabricated from each of a plurality of polymer hollow fiber membranes comprising a module.

23. The mixed-matrix membrane of claim 22 that is a 6FDA-DAM/ZIF-8 mixed-matrix hollow fiber membrane.

24. A method for separating a binary gas mixture, comprising:
flowing the binary gas mixture through the mixed-matrix membrane of claim 19.

25. The method of claim 24, wherein the binary gas mixture is a propylene/propane gas mixture.

* * * * *